US009839609B2

(12) United States Patent
Cozean et al.

(10) Patent No.: US 9,839,609 B2
(45) Date of Patent: Dec. 12, 2017

(54) DIMETHYL SULFOXIDE (DMSO) AND METHYLSULFONYLMETHANE (MSM) FORMULATIONS TO TREAT OSTEOARTHRITIS

(75) Inventors: Colette Cozean, Lake Forest, CA (US); Jesse Cozean, Lake Forest, CA (US); Rodney Benjamin, Vancouver, WA (US); Anthony Keller, Ashland, OR (US)

(73) Assignee: Abela Pharmaceuticals, Inc., Lake Forest, CA (US)

(*) Notice: Subject to any disclaimer, the term of this patent is extended or adjusted under 35 U.S.C. 154(b) by 0 days.

(21) Appl. No.: 13/503,626

(22) PCT Filed: Oct. 29, 2010

(86) PCT No.: PCT/US2010/054870
§ 371 (c)(1),
(2), (4) Date: Apr. 23, 2012

(87) PCT Pub. No.: WO2011/053874
PCT Pub. Date: May 5, 2011

(65) Prior Publication Data
US 2012/0207827 A1    Aug. 16, 2012

Related U.S. Application Data

(60) Provisional application No. 61/256,935, filed on Oct. 30, 2009, provisional application No. 61/319,203, filed on Mar. 30, 2010.

(51) Int. Cl.
*A61K 31/10* (2006.01)
*A61K 9/28* (2006.01)
*A61K 9/48* (2006.01)
*A61P 17/00* (2006.01)
*A61P 19/02* (2006.01)
*A61K 9/00* (2006.01)
*A61K 45/06* (2006.01)
*A61K 31/133* (2006.01)
*A61K 31/17* (2006.01)
*A61K 31/4409* (2006.01)
*A61K 31/496* (2006.01)
*A61K 31/4965* (2006.01)
*A61K 31/7036* (2006.01)

(52) U.S. Cl.
CPC .......... *A61K 9/0053* (2013.01); *A61K 9/0014* (2013.01); *A61K 31/10* (2013.01); *A61K 31/133* (2013.01); *A61K 31/17* (2013.01); *A61K 31/4409* (2013.01); *A61K 31/496* (2013.01); *A61K 31/4965* (2013.01); *A61K 31/7036* (2013.01); *A61K 45/06* (2013.01)

(58) Field of Classification Search
CPC .... A61K 9/0053; A61K 9/0014; A61K 31/10; A61K 45/06; A61K 31/133; A61K 31/4965; A61K 2300/00
See application file for complete search history.

(56) References Cited

U.S. PATENT DOCUMENTS

| 2,638,179 A | 5/1953 | Yard |
| 3,334,012 A | 8/1967 | Herschler |
| 3,361,555 A | 1/1968 | Herschler |
| 3,393,080 A | 7/1968 | Erdi et al. |
| 3,419,619 A | 12/1968 | Soder et al. |
| 3,482,572 A | 12/1969 | Grosclaude et al. |
| 3,527,863 A | 9/1970 | Weichselbaum |
| 3,549,770 A | 12/1970 | Herschler et al. |
| 3,549,771 A | 12/1970 | Herschler |
| 3,551,554 A | 12/1970 | Herschler |
| 3,558,434 A | 1/1971 | Herschler |
| 3,573,214 A | 3/1971 | Kollonitsch |
| 3,592,936 A | 7/1971 | Marcus et al. |
| 3,654,165 A | 4/1972 | Bryant et al. |
| 3,675,654 A | 7/1972 | Baker et al. |
| 3,690,808 A | 9/1972 | St. Pierre |
| 3,711,606 A | 1/1973 | Herschler |
| 3,740,420 A | 6/1973 | Herschler et al. |
| 3,757,495 A | 9/1973 | Sievers |
| 3,773,838 A | 11/1973 | Andruski et al. |

(Continued)

FOREIGN PATENT DOCUMENTS

| CA | 2 617 934 | 2/2007 |
| EP | 0 827 744 | 3/1998 |

(Continued)

OTHER PUBLICATIONS

Aleksevich Ial, Piletskaia IG, Nikonorova VP. *Increase in the sensitivity of the microflora of pathological gingival pockets to streptomycin under the influence of dimexide and trypsin*. Mikrobiol Zh. Nov.-Dec. 1973; 35(6):766-9.
Baer P, Thomas L, Shainhouse JZ. Treatment of osteoarthritis of the knee with a topical diclofenac solution: a randomized, controlled 6-week trial. BMC Musculoskeletal Disord. 2005; 6:44.
Barrager, et al. A Multicentered, Open-Label Trial on the Safety and Efficacy of Methylsulfonylmethane in the Treatment of Seasonal Allergic Rhinitis, The Journal of Alternative and Complementary Medicine, vol. 8, No. 2, 2002, pp. 167-173.
Berry et al. *Natural Gas Odorants Desulfurization*, (2004) AlChE Annual National Meeting, Austin, Texas, Nov. 7-12.
Blumenthal L, Fuchs M. *The Clinical Use of Dimethyl Sulfoxide on Various Headaches, Musculoskeletal and Other General Medical Disorders*. Annals New York Academy of Sciences 1967:572-585.

(Continued)

*Primary Examiner* — Mina Haghighatian
(74) *Attorney, Agent, or Firm* — Sheppard Mullin Richter & Hampton LLP

(57) ABSTRACT

Embodiments of the invention relate generally to the use of formulations comprising DMSO and MSM to treat arthritis (such as osteoarthritis), pain, inflammation, and/or degeneration. DMSO and MSM formulations are administered orally and/or topically in several embodiments and provide effective treatment of both chronic and acute symptoms of arthritis (e.g., osteoarthritis), pain, inflammation, and/or degeneration. Solid forms of DMSO are provided in several embodiments.

4 Claims, 2 Drawing Sheets

(56) References Cited

U.S. PATENT DOCUMENTS

| | | |
|---|---|---|
| 3,790,682 A | 2/1974 | Herschler et al. |
| 3,823,676 A | 7/1974 | Cook et al. |
| 3,852,408 A | 12/1974 | Ewan et al. |
| 3,861,894 A | 1/1975 | Marsh |
| 3,881,003 A | 4/1975 | Rehm |
| 3,948,617 A | 4/1976 | Withorn |
| 3,972,962 A | 8/1976 | Williams et al. |
| 3,976,747 A | 8/1976 | Shale et al. |
| 3,988,129 A | 10/1976 | Fornoff et al. |
| 3,996,295 A | 12/1976 | Goeb |
| 4,015,025 A | 3/1977 | Szczesniak |
| 4,112,946 A | 9/1978 | Herschler |
| 4,125,589 A | 11/1978 | deVries |
| 4,129,122 A | 12/1978 | Dout et al. |
| 4,169,550 A | 10/1979 | Williams |
| 4,177,267 A | 12/1979 | Herschler |
| 4,194,628 A | 3/1980 | Campos |
| 4,202,676 A | 5/1980 | Pelosi, Jr. et al. |
| 4,212,392 A | 7/1980 | McKenzie |
| 4,225,381 A | 9/1980 | Ishikawa et al. |
| 4,252,054 A | 2/1981 | Bakels |
| 4,256,728 A | 3/1981 | Nishino et al. |
| 4,277,450 A | 7/1981 | Dilworth |
| 4,296,104 A | 10/1981 | Herschler |
| 4,296,130 A | 10/1981 | Herschler |
| 4,307,067 A | 12/1981 | Tagawa et al. |
| 4,309,393 A | 1/1982 | Nguyen |
| 4,316,795 A | 2/1982 | Mooi |
| 4,333,922 A | 6/1982 | Herschler |
| 4,335,148 A | 6/1982 | Vidal et al. |
| 4,341,675 A | 7/1982 | Nakamura |
| 4,350,245 A | 9/1982 | Elstner |
| 4,357,288 A | 11/1982 | Oas et al. |
| 4,369,190 A | 1/1983 | Schulte |
| 4,372,915 A | 2/1983 | Neti et al. |
| 4,413,109 A | 11/1983 | Haas |
| 4,424,330 A | 1/1984 | Raviola |
| 4,469,702 A | 9/1984 | Schulte |
| 4,477,469 A | 10/1984 | Herschler |
| 4,491,563 A | 1/1985 | Reusser et al. |
| 4,493,930 A | 1/1985 | Klayman et al. |
| 4,497,824 A | 2/1985 | Schulte |
| 4,505,708 A | 3/1985 | Gajewski et al. |
| 4,510,292 A | 4/1985 | Chiba et al. |
| 4,512,245 A | 4/1985 | Goldman |
| 4,514,421 A | 4/1985 | Herschler |
| 4,545,414 A | 10/1985 | Baum |
| 4,550,010 A | 10/1985 | Chelu |
| 4,559,329 A | 12/1985 | Herschler |
| 4,568,547 A | 2/1986 | Herschler |
| 4,575,515 A | 3/1986 | Sandborn |
| 4,591,497 A | 5/1986 | Naito et al. |
| 4,595,102 A | 6/1986 | Cianci et al. |
| 4,600,002 A | 7/1986 | Maryyanek et al. |
| 4,616,039 A | 10/1986 | Herschler |
| 4,616,064 A | 10/1986 | Zukosky et al. |
| 4,622,221 A | 11/1986 | Schleppnik |
| 4,626,530 A | 12/1986 | Schulte |
| 4,634,588 A | 1/1987 | Moroe |
| 4,642,177 A | 2/1987 | Mester et al. |
| 4,652,557 A | 3/1987 | Sandborn |
| 4,655,148 A | 4/1987 | Winship |
| 4,656,094 A | 4/1987 | Kojima et al. |
| 4,684,380 A | 8/1987 | Leichnitz |
| 4,686,204 A | 8/1987 | Mester et al. |
| 4,710,353 A | 12/1987 | Tanaka et al. |
| 4,719,105 A | 1/1988 | Schleppnik |
| 4,721,813 A | 1/1988 | Mark et al. |
| 4,725,290 A | 2/1988 | Ohlmeyer et al. |
| 4,728,712 A | 3/1988 | Singh et al. |
| 4,729,835 A | 3/1988 | McNeillie et al. |
| 4,737,173 A | 4/1988 | Kudirka et al. |
| 4,747,845 A | 5/1988 | Korol |
| 4,751,241 A | 6/1988 | Motoyama et al. |
| 4,778,697 A | 10/1988 | Genske et al. |
| 4,784,909 A | 11/1988 | Emi et al. |
| 4,796,790 A | 1/1989 | Hamilton |
| 4,797,274 A | 1/1989 | Miki et al. |
| 4,803,047 A | 2/1989 | Pluim, Jr. |
| 4,830,718 A | 5/1989 | Stauffer |
| 4,834,721 A | 5/1989 | Onohara et al. |
| 4,850,268 A | 7/1989 | Saito et al. |
| 4,863,687 A | 9/1989 | Stevens et al. |
| 4,863,748 A | 9/1989 | Herschler |
| 4,887,751 A | 12/1989 | Lehman |
| 4,902,489 A | 2/1990 | Watanabe |
| 4,902,558 A | 2/1990 | Henriksen |
| 4,904,520 A | 2/1990 | Dumas et al. |
| 4,910,803 A | 3/1990 | Cukier |
| 4,911,691 A | 3/1990 | Aniuk et al. |
| 4,914,135 A | 4/1990 | Herschler |
| 4,916,767 A | 4/1990 | Uetake et al. |
| 4,919,925 A | 4/1990 | Ueda et al. |
| 4,931,276 A | 6/1990 | Franco et al. |
| 4,933,169 A | 6/1990 | Shanbrom |
| 4,937,115 A | 6/1990 | Leatherman |
| 4,940,405 A | 7/1990 | Kelly |
| 4,940,658 A | 7/1990 | Allen et al. |
| 4,941,991 A | 7/1990 | Rajamannan |
| 4,946,720 A | 8/1990 | Oishi et al. |
| 4,948,643 A | 8/1990 | Mueller |
| 4,948,787 A | 8/1990 | Chen et al. |
| 4,956,183 A | 9/1990 | Miki et al. |
| 4,973,605 A | 11/1990 | Herschler |
| 4,978,687 A | 12/1990 | Pascuchi |
| 4,980,045 A | 12/1990 | Krishna et al. |
| 4,988,505 A | 1/1991 | Watanabe et al. |
| 4,990,311 A | 2/1991 | Hirai et al. |
| 4,994,245 A | 2/1991 | Murray et al. |
| 5,001,794 A | 3/1991 | Uetake et al. |
| 5,006,510 A | 4/1991 | Ellis |
| 5,007,999 A | 4/1991 | Chin |
| 5,032,613 A | 7/1991 | Watson |
| 5,041,273 A | 8/1991 | Rock |
| 5,049,159 A | 9/1991 | Yamaji et al. |
| 5,049,163 A | 9/1991 | Huang et al. |
| 5,055,279 A | 10/1991 | Hirt et al. |
| 5,059,477 A | 10/1991 | Henriksen |
| 5,070,597 A | 12/1991 | Holt et al. |
| 5,071,622 A | 12/1991 | Dunson, Jr. |
| 5,071,686 A | 12/1991 | Genske et al. |
| 5,071,878 A | 12/1991 | Herschler |
| 5,083,558 A | 1/1992 | Thomas et al. |
| 5,086,804 A | 2/1992 | Ngai |
| 5,087,673 A | 2/1992 | Watanabe et al. |
| 5,091,180 A | 2/1992 | Walker et al. |
| 5,117,821 A | 6/1992 | White |
| 5,133,788 A | 7/1992 | Backus |
| 5,135,904 A | 8/1992 | Kamiya et al. |
| 5,139,831 A | 8/1992 | Mueller |
| 5,143,831 A | 9/1992 | Wong et al. |
| 5,145,657 A | 9/1992 | Kobayashi et al. |
| 5,149,576 A | 9/1992 | Potts et al. |
| 5,152,814 A | 10/1992 | Nelson |
| 5,160,707 A | 11/1992 | Murray et al. |
| 5,169,217 A | 12/1992 | Orchard et al. |
| 5,182,016 A | 1/1993 | Funkenbusch et al. |
| 5,183,656 A | 2/1993 | Uesaka et al. |
| 5,190,640 A | 3/1993 | Roof et al. |
| 5,192,272 A | 3/1993 | Faure |
| 5,192,342 A | 3/1993 | Baron et al. |
| 5,192,498 A | 3/1993 | Chen et al. |
| 5,199,263 A | 4/1993 | Green et al. |
| 5,207,303 A | 5/1993 | Oswalt et al. |
| 5,213,680 A | 5/1993 | Kremer et al. |
| 5,218,036 A | 6/1993 | Kagawa et al. |
| 5,218,147 A | 6/1993 | Shaw |
| 5,240,478 A | 8/1993 | Messina |
| 5,260,090 A | 11/1993 | Isao |
| 5,269,294 A | 12/1993 | Rogozinski |
| 5,290,331 A | 3/1994 | Miles et al. |
| 5,335,373 A | 8/1994 | Dangman et al. |
| 5,336,431 A | 8/1994 | Richards et al. |
| 5,344,529 A | 9/1994 | Stauffer |

(56) References Cited

U.S. PATENT DOCUMENTS

| | | |
|---|---|---|
| 5,356,709 A | 10/1994 | Woo et al. |
| 5,358,443 A | 10/1994 | Mitchell et al. |
| 5,360,468 A | 11/1994 | Schubert |
| 5,409,769 A | 4/1995 | Fukumoto et al. |
| 5,415,180 A | 5/1995 | Horan |
| 5,419,812 A | 5/1995 | Beal |
| 5,439,454 A | 8/1995 | Lo et al. |
| 5,441,729 A | 8/1995 | Salce et al. |
| 5,458,848 A | 10/1995 | Burgaud |
| 5,458,861 A | 10/1995 | Buchanan et al. |
| 5,460,625 A | 10/1995 | Johnson |
| 5,466,757 A | 11/1995 | Watanabe et al. |
| 5,480,860 A | 1/1996 | Dillon |
| 5,486,387 A | 1/1996 | Mueller |
| 5,487,766 A | 1/1996 | Vannier |
| 5,494,587 A | 2/1996 | Morlec et al. |
| 5,512,144 A | 4/1996 | Stauffer |
| 5,516,526 A | 5/1996 | De la Torre |
| 5,521,268 A | 5/1996 | Ghyzel et al. |
| 5,531,987 A | 7/1996 | Bauer et al. |
| 5,538,545 A | 7/1996 | Dauber et al. |
| 5,562,127 A | 10/1996 | Fanselow et al. |
| 5,569,679 A | 10/1996 | Jacob |
| 5,578,540 A | 11/1996 | Banzi et al. |
| 5,582,865 A | 12/1996 | Rezuke et al. |
| 5,584,986 A | 12/1996 | Bartholic |
| 5,603,696 A | 2/1997 | Williams et al. |
| 5,605,635 A | 2/1997 | David |
| 5,607,647 A | 3/1997 | Kinkead |
| 5,616,408 A | 4/1997 | Oleszczuk et al. |
| 5,620,760 A | 4/1997 | Galimberti et al. |
| 5,624,649 A | 4/1997 | Gal |
| 5,626,820 A | 5/1997 | Rezuke et al. |
| 5,650,329 A | 7/1997 | Warner |
| 5,654,061 A | 8/1997 | Visioli |
| 5,658,801 A | 8/1997 | Poissant et al. |
| 5,667,799 A | 9/1997 | Caldwell et al. |
| 5,703,152 A | 12/1997 | Ohama |
| 5,712,044 A | 1/1998 | Fanselow et al. |
| 5,725,893 A | 3/1998 | Pittet et al. |
| 5,753,696 A | 5/1998 | Shealy et al. |
| 5,761,362 A | 6/1998 | Yang et al. |
| 5,779,679 A | 7/1998 | Shaw |
| 5,783,269 A | 7/1998 | Heilmann et al. |
| 5,789,046 A | 8/1998 | Mueller |
| 5,792,505 A | 8/1998 | Fulger et al. |
| 5,803,130 A | 9/1998 | Robben et al. |
| 5,803,249 A | 9/1998 | Harsanyi, Jr. et al. |
| 5,843,420 A | 12/1998 | Bauer et al. |
| 5,849,846 A | 12/1998 | Chen et al. |
| 5,861,096 A | 1/1999 | Mason et al. |
| 5,871,562 A | 2/1999 | Culoso |
| 5,885,566 A | 3/1999 | Goldberg |
| 5,891,508 A | 4/1999 | Barnum |
| 5,919,877 A | 7/1999 | Tanaglia |
| 5,928,744 A | 7/1999 | Heilmann et al. |
| 5,931,303 A | 8/1999 | Salvadori |
| 5,935,412 A | 8/1999 | Brainard, II |
| 5,935,547 A | 8/1999 | LeComte et al. |
| 5,948,398 A | 9/1999 | Hanamoto et al. |
| 5,958,502 A | 9/1999 | Fulger et al. |
| 5,965,276 A | 10/1999 | Shlenker et al. |
| 5,967,061 A | 10/1999 | Ashworth et al. |
| 5,972,993 A | 10/1999 | Ptchelintsev |
| 5,989,497 A | 11/1999 | Labonte, Jr. |
| 5,998,019 A | 12/1999 | Rosenbaum et al. |
| 6,007,520 A | 12/1999 | Sudo |
| 6,010,666 A | 1/2000 | Kurokawa et al. |
| 6,012,586 A | 1/2000 | Misra |
| 6,015,536 A | 1/2000 | Lokkesmoe et al. |
| 6,030,494 A | 2/2000 | Hupa et al. |
| 6,042,640 A | 3/2000 | Isganitis et al. |
| 6,045,596 A | 4/2000 | Holland, Jr. et al. |
| 6,048,733 A | 4/2000 | Machino et al. |
| 6,057,018 A | 5/2000 | Schmidt |
| 6,060,083 A | 5/2000 | Dorr et al. |
| 6,060,152 A | 5/2000 | Murchie |
| D427,299 S | 6/2000 | Haslebacher |
| 6,070,578 A | 6/2000 | Baughman et al. |
| 6,071,905 A | 6/2000 | Krasnov et al. |
| 6,077,335 A | 6/2000 | Schneider et al. |
| 6,090,076 A | 7/2000 | Lane, Jr. |
| 6,094,549 A | 7/2000 | Hiraoka et al. |
| 6,099,607 A | 8/2000 | Haslebacher |
| 6,106,502 A | 8/2000 | Richmond |
| 6,106,596 A | 8/2000 | Haramoto et al. |
| 6,110,176 A | 8/2000 | Shapira |
| 6,114,586 A | 9/2000 | Devaux et al. |
| D431,353 S | 10/2000 | Mellin |
| D431,902 S | 10/2000 | Mellin |
| 6,183,708 B1 | 2/2001 | Hei et al. |
| 6,183,758 B1 | 2/2001 | Scott |
| 6,197,288 B1 | 3/2001 | Mankoo |
| 6,207,106 B1 | 3/2001 | Kurokawa et al. |
| 6,221,325 B1 | 4/2001 | Brown et al. |
| 6,228,960 B1 | 5/2001 | Tanaglia |
| 6,238,767 B1 | 5/2001 | McCormack et al. |
| 6,248,733 B1 | 6/2001 | Landgrebe et al. |
| 6,261,655 B1 | 7/2001 | Rosenbaum et al. |
| 6,267,941 B1 | 7/2001 | Sata |
| 6,277,344 B1 | 8/2001 | Hei et al. |
| 6,294,161 B1 | 9/2001 | Hiramoto et al. |
| 6,303,200 B1 | 10/2001 | Woo et al. |
| 6,312,713 B1 | 11/2001 | Korol et al. |
| 6,318,075 B1 | 11/2001 | Gunther et al. |
| 6,348,177 B1 | 2/2002 | Bartley et al. |
| 6,349,826 B1 | 2/2002 | Kapik et al. |
| 6,365,099 B1 | 4/2002 | Castrantas et al. |
| 6,403,642 B1 | 6/2002 | Berg |
| 6,403,739 B1 | 6/2002 | Tanaglia et al. |
| 6,406,767 B1 | 6/2002 | Mueller |
| 6,412,639 B1 | 7/2002 | Hickey |
| 6,414,194 B1 | 7/2002 | Bloom, Jr. et al. |
| 6,416,772 B1 | 7/2002 | Van Engelen et al. |
| 6,418,932 B2 | 7/2002 | Paschal, Jr. et al. |
| 6,426,112 B1 | 7/2002 | Boatright |
| 6,426,370 B1 | 7/2002 | Hofschneider |
| 6,432,891 B1 | 8/2002 | O'Connor |
| 6,440,391 B1 | 8/2002 | Jacob |
| 6,454,097 B1 | 9/2002 | Blanco |
| 6,458,828 B1 | 10/2002 | Sakurai et al. |
| 6,460,702 B2 | 10/2002 | Hammond |
| 6,461,631 B1 | 10/2002 | Dunn et al. |
| 6,465,068 B1 | 10/2002 | Patel et al. |
| 6,468,259 B1 | 10/2002 | Loretti et al. |
| 6,475,466 B1 | 11/2002 | Ricci et al. |
| 6,479,150 B1 | 11/2002 | Liu et al. |
| 6,479,488 B1 | 11/2002 | Di-Fabio et al. |
| 6,482,377 B2 | 11/2002 | Bartley et al. |
| 6,495,096 B1 | 12/2002 | Hamaguchi et al. |
| 6,528,080 B2 | 3/2003 | Dunn et al. |
| 6,531,111 B1 | 3/2003 | Whalen, II et al. |
| 6,552,231 B2 | 4/2003 | Jones et al. |
| 6,562,447 B2 | 5/2003 | Wu et al. |
| 6,579,444 B2 | 6/2003 | Feimer et al. |
| 6,579,543 B1 | 6/2003 | McClung |
| 6,599,472 B1 | 7/2003 | Hudson |
| 6,620,911 B1 | 9/2003 | Petit et al. |
| 6,632,842 B2 | 10/2003 | Chaudry et al. |
| 6,638,605 B1 | 10/2003 | Ankuda, Jr. et al. |
| 6,639,110 B2 | 10/2003 | Fremy |
| 6,649,193 B1 | 11/2003 | Colic |
| 6,652,845 B2 | 11/2003 | Hu et al. |
| 6,653,352 B2 | 11/2003 | Barr et al. |
| 6,656,723 B1 | 12/2003 | Phillips |
| 6,663,679 B1 | 12/2003 | Duncan |
| 6,680,194 B1 | 1/2004 | Turner |
| 6,706,257 B1 | 3/2004 | McCook et al. |
| 6,718,914 B2 | 4/2004 | Riddles |
| 6,722,295 B2 | 4/2004 | Zauderer |
| 6,723,349 B1 | 4/2004 | Hill et al. |
| 6,723,399 B2 | 4/2004 | Chundury et al. |
| 6,734,263 B2 | 5/2004 | Eadara et al. |
| 6,737,031 B2 | 5/2004 | Beal et al. |

(56) References Cited

U.S. PATENT DOCUMENTS

| | | |
|---|---|---|
| 6,737,089 B2 | 5/2004 | Wadsworth et al. |
| 6,743,523 B1 | 6/2004 | Woo et al. |
| 6,743,951 B2 | 6/2004 | Fremy |
| 6,761,169 B2 | 7/2004 | Eswarappa |
| 6,761,912 B2 | 7/2004 | Forusz et al. |
| 6,764,566 B1 | 7/2004 | Griesbach, III et al. |
| 6,783,004 B1 | 8/2004 | Rinner |
| RE38,597 E | 9/2004 | Lane, Jr. |
| 6,796,958 B2 | 9/2004 | Chen et al. |
| 6,797,042 B2 | 9/2004 | LaFerriere et al. |
| 6,822,015 B2 | 11/2004 | Muraki |
| 6,830,794 B2 | 12/2004 | Cartledge et al. |
| 6,844,430 B2 | 1/2005 | Pesce et al. |
| 6,846,535 B2 | 1/2005 | De Groot et al. |
| 6,858,192 B2 | 2/2005 | Graham et al. |
| 6,872,241 B2 | 3/2005 | Soane et al. |
| 6,881,419 B2 | 4/2005 | Lovett |
| 6,884,797 B2 | 4/2005 | Hofmann |
| 6,890,373 B2 | 5/2005 | Nemoto et al. |
| 6,902,714 B2 | 6/2005 | Skaarup Jensen et al. |
| 6,908,885 B2 | 6/2005 | Bengs et al. |
| 6,927,305 B2 | 8/2005 | Choudary et al. |
| 7,057,016 B2 | 6/2006 | Cerletti |
| 7,203,974 B2 | 4/2007 | Jones et al. |
| 7,282,224 B1 | 10/2007 | Roederer |
| 7,371,407 B2 | 5/2008 | Farmer |
| 7,381,521 B2 | 6/2008 | Whitaker |
| 7,955,418 B2 | 6/2011 | Claussen et al. |
| 8,298,320 B2 | 10/2012 | Cozean |
| 8,435,224 B2 | 5/2013 | Claussen et al. |
| 8,440,001 B2 | 5/2013 | Cozean |
| 8,480,797 B2 | 7/2013 | Cozean et al. |
| 8,673,061 B2 | 3/2014 | Cozean et al. |
| 2001/0005766 A1 | 6/2001 | Fremy |
| 2001/0018095 A1 | 8/2001 | Shlenker et al. |
| 2001/0047038 A1 | 11/2001 | Moorman et al. |
| 2002/0015762 A1 | 2/2002 | Quinlan |
| 2002/0025983 A1 | 2/2002 | Horrobin |
| 2002/0032131 A1 | 3/2002 | O'Connor |
| 2002/0043501 A1 | 4/2002 | Irvine |
| 2002/0090398 A1 | 7/2002 | Dunn et al. |
| 2002/0110549 A1 | 8/2002 | Till |
| 2002/0115729 A1 | 8/2002 | Yang |
| 2002/0131933 A1 | 9/2002 | Delmotte |
| 2002/0133100 A1 | 9/2002 | Paschal, Jr. et al. |
| 2002/0151753 A1 | 10/2002 | Fremy |
| 2002/0156326 A1 | 10/2002 | Fremy |
| 2002/0179647 A1 | 12/2002 | Hall et al. |
| 2002/0182263 A1 | 12/2002 | Stenti et al. |
| 2003/0017183 A1 | 1/2003 | Pollock |
| 2003/0032616 A1 | 2/2003 | Moskowitz et al. |
| 2003/0082321 A1 | 5/2003 | Kennedy et al. |
| 2003/0085170 A1 | 5/2003 | Scranton et al. |
| 2003/0108810 A1 | 6/2003 | Williamson et al. |
| 2003/0109495 A1 | 6/2003 | Kretschmer |
| 2003/0118672 A1 | 6/2003 | McPeak et al. |
| 2003/0133959 A1 | 7/2003 | Shacknai et al. |
| 2003/0152862 A1 | 8/2003 | Williamson et al. |
| 2003/0157006 A1 | 8/2003 | Hei et al. |
| 2003/0167033 A1 | 9/2003 | Chen et al. |
| 2003/0190266 A1 | 10/2003 | Tsurumi |
| 2003/0203009 A1 | 10/2003 | MacDonald |
| 2003/0203484 A1 | 10/2003 | Black et al. |
| 2003/0226443 A1 | 12/2003 | Rajagopalan et al. |
| 2004/0016410 A1 | 1/2004 | Riddles |
| 2004/0039066 A1 | 2/2004 | Crea |
| 2004/0048376 A1 | 3/2004 | Chabot et al. |
| 2004/0057972 A2 | 3/2004 | Shacknai et al. |
| 2004/0074212 A1 | 4/2004 | Yachi et al. |
| 2004/0081673 A1 | 4/2004 | Rayner et al. |
| 2004/0082667 A1 | 4/2004 | McCadden et al. |
| 2004/0086888 A1 | 5/2004 | Kornblith et al. |
| 2004/0087669 A1 | 5/2004 | Hausmanns et al. |
| 2004/0105943 A1 | 6/2004 | Hoerner et al. |
| 2004/0115818 A1 | 6/2004 | Puri et al. |
| 2004/0121023 A1 | 6/2004 | Stevens |
| 2004/0131806 A1 | 7/2004 | Barmore et al. |
| 2004/0137136 A1 | 7/2004 | Zheng et al. |
| 2004/0151826 A1 | 8/2004 | Milligan |
| 2004/0154220 A1 | 8/2004 | Holcomb |
| 2004/0156742 A1 | 8/2004 | Milan et al. |
| 2004/0157802 A1 | 8/2004 | Horwitz et al. |
| 2004/0186316 A1 | 9/2004 | Choudary et al. |
| 2004/0197339 A1 | 10/2004 | Brown |
| 2004/0213755 A1 | 10/2004 | Hochwalt et al. |
| 2004/0213774 A9 | 10/2004 | Till |
| 2004/0219126 A1 | 11/2004 | Seto et al. |
| 2004/0242818 A1 | 12/2004 | Williamson et al. |
| 2004/0265291 A1 | 12/2004 | Drake et al. |
| 2005/0025840 A1 | 2/2005 | Revnolds |
| 2005/0031651 A1 | 2/2005 | Gervais et al. |
| 2005/0031761 A1 | 2/2005 | Brucker et al. |
| 2005/0035062 A1 | 2/2005 | Hiltzik et al. |
| 2005/0054875 A1 | 3/2005 | Hei et al. |
| 2005/0058630 A1 | 3/2005 | Harris et al. |
| 2005/0069598 A1 | 3/2005 | Ribnicky et al. |
| 2005/0084412 A1 | 4/2005 | MacDonald et al. |
| 2005/0084438 A1 | 4/2005 | Do et al. |
| 2005/0084464 A1 | 4/2005 | McGrath et al. |
| 2005/0084474 A1 | 4/2005 | Wu et al. |
| 2005/0092070 A1 | 5/2005 | Bhatti |
| 2005/0092761 A1 | 5/2005 | Marganski et al. |
| 2005/0095653 A1 | 5/2005 | Goldstein et al. |
| 2005/0112085 A1 | 5/2005 | MacDonald et al. |
| 2005/0112176 A1 | 5/2005 | Dopson et al. |
| 2005/0112177 A1 | 5/2005 | Dopson et al. |
| 2005/0115895 A1 | 6/2005 | Simpson et al. |
| 2005/0136082 A1 | 6/2005 | Soane et al. |
| 2005/0136125 A1 | 6/2005 | Roth |
| 2005/0142096 A1 | 6/2005 | Wegner |
| 2005/0147692 A1 | 7/2005 | Roth |
| 2005/0158406 A1 | 7/2005 | McPeak et al. |
| 2005/0158424 A1 | 7/2005 | Nakano et al. |
| 2005/0169826 A1 | 8/2005 | Li |
| 2005/0176778 A1 | 8/2005 | Vermeer |
| 2005/0181048 A1 | 8/2005 | Romero |
| 2005/0182076 A1 | 8/2005 | Pacheco et al. |
| 2005/0187124 A1 | 8/2005 | Li et al. |
| 2005/0191343 A1 | 9/2005 | Liang |
| 2005/0215515 A1 | 9/2005 | Bucolo et al. |
| 2005/0222275 A1 | 10/2005 | Gabizon et al. |
| 2005/0224409 A1 | 10/2005 | Harshman et al. |
| 2005/0226827 A1 | 10/2005 | Ho |
| 2005/0227910 A1 | 10/2005 | Yang et al. |
| 2005/0260306 A1 | 11/2005 | Baldus |
| 2005/0261257 A1 | 11/2005 | Vermeer |
| 2005/0265979 A1 | 12/2005 | Aoki et al. |
| 2005/0266064 A1 | 12/2005 | McCarthy |
| 2005/0281883 A1 | 12/2005 | Daniloff et al. |
| 2006/0003069 A1 | 1/2006 | Zheng et al. |
| 2006/0006120 A1 | 1/2006 | Chen et al. |
| 2006/0006121 A1 | 1/2006 | Simpson et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0052438 A1 | 3/2006 | Ho et al. |
| 2006/0121613 A1 | 6/2006 | Havens |
| 2006/0127508 A1 | 6/2006 | Larkins |
| 2006/0143767 A1 | 7/2006 | Yang et al. |
| 2006/0166948 A1 | 7/2006 | Vermeer |
| 2006/0177398 A1 | 8/2006 | McCook et al. |
| 2006/0194759 A1 | 8/2006 | Eidelson |
| 2006/0210646 A1 | 9/2006 | Oku et al. |
| 2006/0281822 A1 | 12/2006 | Appleton |
| 2007/0025950 A1 | 2/2007 | Elson |
| 2007/0028772 A1 | 2/2007 | Jain et al. |
| 2007/0048386 A1 | 3/2007 | Mallozzi, Sr. et al. |
| 2007/0180544 A1 | 8/2007 | Taylor |
| 2007/0183936 A1 | 8/2007 | Newsam et al. |
| 2007/0237816 A1* | 10/2007 | Finkelstein ............ A61K 31/10 424/464 |
| 2007/0243146 A1 | 10/2007 | Klock |
| 2007/0264212 A1 | 11/2007 | Ho |
| 2007/0270358 A1 | 11/2007 | Paoliambrosi |

(56) References Cited

U.S. PATENT DOCUMENTS

| | | |
|---|---|---|
| 2007/0292493 A1 | 12/2007 | Brierre |
| 2008/0038219 A1 | 2/2008 | Mosbaugh et al. |
| 2008/0076831 A1 | 3/2008 | Goetz |
| 2008/0102107 A1 | 5/2008 | Lewellyn et al. |
| 2008/0146458 A1 | 6/2008 | Hollingsworth et al. |
| 2008/0193427 A1 | 8/2008 | Kaesler et al. |
| 2008/0228161 A1 | 9/2008 | Claussen et al. |
| 2008/0249082 A1 | 10/2008 | Hollander |
| 2008/0251081 A1 | 10/2008 | Claussen et al. |
| 2008/0260871 A1 | 10/2008 | Fruitman |
| 2008/0274153 A1 | 11/2008 | Farmer |
| 2008/0275015 A1 | 11/2008 | Potter |
| 2008/0300311 A1 | 12/2008 | Kisak et al. |
| 2008/0317680 A1 | 12/2008 | Dueva-Koganov et al. |
| 2008/0319092 A1 | 12/2008 | Singh et al. |
| 2009/0104235 A1* | 4/2009 | Exner ............ A61K 9/0031 424/400 |
| 2009/0215888 A1 | 8/2009 | Jagat et al. |
| 2009/0312273 A1 | 12/2009 | De la Torre |
| 2009/0324784 A1 | 12/2009 | McLellan et al. |
| 2011/0105623 A1 | 5/2011 | Benjamin et al. |
| 2011/0136210 A1 | 6/2011 | Benjamin et al. |
| 2011/0203583 A1 | 8/2011 | Cozean |
| 2011/0203585 A1 | 8/2011 | Cozean |
| 2013/0018059 A1 | 1/2013 | Jacob et al. |
| 2013/0045941 A1 | 2/2013 | Cozean et al. |

FOREIGN PATENT DOCUMENTS

| | | |
|---|---|---|
| EP | 0 976 726 | 2/2000 |
| GB | 2 028 162 | 12/1979 |
| JP | 2003-306446 | 10/2003 |
| JP | 2005-0270589 | 10/2005 |
| JP | 2005 330199 | 12/2005 |
| RU | 2035909 | 5/1995 |
| WO | WO 85/00108 | 1/1985 |
| WO | WO 94/05272 | 3/1994 |
| WO | WO 94/05273 | 3/1994 |
| WO | WO/95/03753 | 2/1995 |
| WO | WO 95/03753 | 2/1995 |
| WO | WO 00/64868 | 11/2000 |
| WO | WO 01/73096 | 10/2001 |
| WO | WO 03/015760 | 2/2003 |
| WO | WO 03/101415 | 12/2003 |
| WO | WO 2004/064877 | 8/2004 |
| WO | WO 2004/067013 | 8/2004 |
| WO | WO 2004/093541 | 11/2004 |
| WO | WO 2004/100896 | 11/2004 |
| WO | WO 2005/054553 | 6/2005 |
| WO | WO 2005/115546 | 12/2005 |
| WO | WO 2005/117913 | 12/2005 |
| WO | WO 2006/129149 | 12/2006 |
| WO | WO 2006/135854 | 12/2006 |
| WO | WO 2007/009245 | 1/2007 |
| WO | WO 2007/016766 | 2/2007 |
| WO | WO 2007/033082 | 3/2007 |
| WO | WO/2007/033082 | 3/2007 |
| WO | WO 2007/033083 | 3/2007 |
| WO | WO/2007/033083 | 3/2007 |
| WO | WO 2007/033180 | 3/2007 |
| WO | WO 2007/049262 | 5/2007 |
| WO | WO 2007/056205 | 5/2007 |
| WO | WO 2007/098591 | 9/2007 |
| WO | WO 2007/126191 | 11/2007 |
| WO | WO 2008/049020 | 4/2008 |
| WO | WO 2008/091704 | 7/2008 |
| WO | WO 2008/098871 | 8/2008 |
| WO | WO 2010/054093 | 5/2010 |
| WO | WO 2010/062721 | 6/2010 |
| WO | WO/2010/062721 | 6/2010 |
| WO | WO 2011/053848 | 5/2011 |
| WO | WO 2011/053854 | 5/2011 |
| WO | WO 2011/053874 | 5/2011 |
| WO | WO 2011/053875 | 5/2011 |
| WO | WO 2011/123695 | 10/2011 |

OTHER PUBLICATIONS

Bookman A, Williams S, Shainhouse J. *Effect of a topical diclofenac solution for relieving symptoms of primary osteoarthritis of the knee: a randomized controlled trial*. CMAJ Aug. 17, 2004; 171(4):333-338.

Brayton CF. *Dimethyl Sulfoxide (DMSO); A Review*. The Cornel Veterinarian. Jan. 1986; 76(1):61-90.

Brechner V, Cohen D, Pretsky I. *Dermal Anesthesia by the Topical Application of Tetracaine Base Dissolved in Dimethyl Sulfoxide*, Annals New York Academy of Sciences. 1967:524-531.

Brien et al. *Systematic review of the nutritional supplements dimethyl sulfoxide (DMSO) and methylsulfonylmethane (MSM) in the treatment of osteoarthritis*. Osteoarthritis and Cartilage (2008) 16:1277-1288.

Brien S, Prescott P, Lewith G. *Meta-analysis of the Related Nutritional Supplements Dimethyl Sulfoxide and Methylsulfonlymethane in the Treatment of Osteoarthritis of the Knee*. eCAM Advance Access published May 27, 2009 in 10 pages.

Brown JH. *Clinical Experience with DMSO in Acute Musculoskeletal Conditions, Comparing a Noncontrolled Series with a Controlled Double Blind Study*. Ann NY Acad Sci 1967; 141(1):496-505.

Cherian L, Robertson C. *L-Arginine and Free Radical Scavengers Increase Cerebral Blood Flow and Brain Tissue Nitric Oxide Concentrations after Controlled Cortical Impact Injury in Rats*. Journal of Neurotrauma, vol. 20, No. 1, 2003; (Jan. 2003), pp. 77-85.

Debi R, et al. *The Role of MSM in Knee Osteoarthritis: A Double Blind, RandomizedProspective Study*. Osteoarthritis and Cartilage (2008) 15 Supplemental C:C231 (426).

Demos C et al. *Dimethyl Sulfoxide in Musculoskeletal Disorders*. Ann NY Acad Sci 1967:517-523.

Eberhardt et al. *DMSO in patients with Active Gonarthrosis. A double-blind, placebo-controlled Phase III Study*. Fortschr Med, Nov. 10, 1995: 113(31):446-450.

Evans MS, Reid KH, Sharp JB. *Dimethylsulfoxide (DMSO) blocks conduction in peripheral nerve C fibers: a possible mechanism of analgesia*. Neuroscience Letters, 150 (1993):145-148.

Feldman WE, Punch JD, Holden PC. *In vivo and in vitro effects of dimethyl sulfoxide on streptomycin-sensitive and—resistant Escherichia coli*. Ann NY Acad Sci, Jan. 27, 1975; 243:269-77.

Florain, *The Solid State Structures of the Dimethylformamide and Dimethylsulfoxide Complexes of Dioxodichloromolybdenum (VI)*, ProQuest, 30-07B (1969), pp. 66.

Glasser D. *Dimethylsulfoxide (DMSO) "resensibilization" as potential chemotherapy for opportunistic mycobacterial disease*. Am Rev Respir Dis. Nov. 1978; 118(5):969-70.

Gorbach IN, Samtsov VS. *Therapeutic possibilities of inhalation of rifampicin with dimexide in phthisiopulmonology*. Probl Tuberk. 1991; (3):34-6.

"Guidance on Medical Device Patient Labeling" accessed Mar. 10, 2010. http://www.fda.gov/MedicalDevices/DeviceRegulationandGuidance/GuidanceDocuments/ucm070782.htm.

Haigler HJ et al. *Comparison of the Analgesic Effects of Dimethyl Sulfoxide and Morphine*, Ann NY Acad Sci 1983; (411):19-27.

Hasegawa T, *Suppressive Effects of Methylsulfonylmethane (MSM) on Type II Collagen-induced Arthritis in DBA/1J Mice*. Jpn Pharmacol Ther 2004; 32 (7):421-427.

Jacob S, Appleton J. *MSM: The Definitive Guide—Chapter 6, 45-54, Part II, Chapter 7, 57-68, Chapter 8, 69-76, Chapter 10, 84-90, Chapter 21, 181-186*. California: Freedom Press, 2003.

Jacob S, Lawrence R, Zucker M, *The Miracle of MSM—The Natural Solution for Pain*. New York: Library of Congress Cataloging-in-Publication Data, 1999.

Jacob SW, Herschler R. *Pharmacology of DMSO*, Cryobiology, 1985, 23(1):14-27.

(56) References Cited

OTHER PUBLICATIONS

Jacob, S.W. and Wood, D.C. *Dimethyl sulfoxide (DMSO): Toxicology, pharmacology, and clinical experience*. Am. J. Surg. 1967; 114(3):414-426.

Jacob et al., Interstitial Cystitis Network—Char Log, Topic: Understanding DMSO; Mar. 28, 2000; The IC Network.

Jagannath C, Reddy VM, Gangadharam PR. *Enhancement of drug susceptibility of multi-drug resistant strains of Mycobacterium tuberculosis by ethambutol and dimethyl sulphoxide*. J Antimicrob Chemother. Mar. 1995; 35(3):381-90.

Jimenez RA, Willkens RF. *Dimethyl Sulphoxide: a perspective of its use in rheumatic diseases*. J Lab Clin Med 1982; 100(4):489-500.

John, H., Laudahn, G. *Clinical Experiences with the Topical Application of DMSO in Orthopedic Diseases: Evaluation of 4,180 Cases*, Annals New York Academy of Sciences, 1967; vol. 141:506-516.

Karlson AG, Ulrich JA, *Stock solutions of rifampin remain stable in dimethylsulfoxide for at least 8 months*, Appl Microbiol. Oct. 1969; 18(4):692-3.

Kim, et al. *Efficacy of Methylsulfonylmethane (MSM) in Osteoarthritis Pain of The Knee: A Pilot Clinical Trial*. Osteoarthritis and Cartilage (2006) 14:286-294.

Knowles R. *Clinical Experience with DMSO in Small Animal Practice*, Annals New York Academy Sciences (1967) 141:478-483.

Kocsis, et al., "Biological Effects of the Metabolites of Dimethyl Sulfoxide", Ann N.Y. Acad. Sci. 243, 104 09 (1975).

Koenen NJ, Haag RF, BiaP, RoseP. *Perkutane therapie bei aktivierter Gonarthrose*. Munch Med Wochenschr 1996; 138 (31-32):534-538.

Kubota et al. *Beneficial effect of L-Arginine for Stroke-like episode in MELAS* Brain and Development, Amsterdam, JL, vol. 26, No. 7, Oct. 1, 2004; pp. 481-483.

Liubinets VI, Kruk MV. *Dimexide in the treatment of endobronchitis in patients with destructive forms of pulmonary tuberculosis*, Zh Ushn Nos Gorl Bolezn. Nov.-Dec. 1969; 29(6):68-71.

Lockie and Norcross. *A Clinical Study on the Effects of Dimethyl Sulfoxide in 103 Patients with Acute and Chronic Musculoskeletal Injuries and Inflammations*, Annals New York Academy Sciences (1967) 141:599-602.

Martin D. and Hauthal H., *Dimethyl Sulfoxide*—Chapter 12. New York: John Wiley & Sons, 1971.

Matsumoto, J. *Clincal Trials of Dimethyl Sulfoxide in Rheumatoid Arthritis Patients in Japan*, Annals New York Academy Sciences. 1967; vol. 141:560-568.

Mitinskaia LA, Iukhimenko NV, Kamaeva VF. *BCG vaccination and increasing the effectiveness of treatment of post-vaccination complications by the use of rifampicin and dimexide*. Probl Tuberk. 1994; (5):4-7.

Mohamaddi F, O'Mara K, Unusual Patient Odor Interfering with Care, Resurrection Medical Center, Chicago, Ill. (1996).

Muller U, Urbanczik R. *Influence of dimethyl sulfoxide (DMSO) on restoring sensitivity of mycobacterial strains resistant to chemotherapeutic compounds*, J Antimicrob Chemother. May 1979; 5(3):326-7.

Murav'ev IuV, Venikova MS, Peskovskaia GN, Riazantseva TA, Sigldin IaA. *Effect of dimethylsulphoxide and dimethyl sulfone*. Patol Fiziol Eksp Ter Mar.-Apr. 1991; (2):37-39.

Nash DR, Steingrube VA. *In vitro drug sensitivity of M. avium-intracellulare complex in the presence and absence of dimethyl sulfoxide*. Microbios. 1982; 35(140):71-8.

Oshima Y, Theodosakis J, Amiel D. *The Effect of Distilled Methylsulfonylmethane (MSM) on Human Chondrocytes in vitro*. World Congress on Osteoarthritis, Ft. Lauderdale, Florida; Osteoarthritis and Cartilage 2007; vol. 15 Supplemental C123:213.

Ostojic et. al. *Laboratory Testing of Cabin Air Filters for the Removal of Reduced-Sulfur Odors*. New Engine Design and Automotive Filtration SAE Special Publications 1998; 1362:41-58.

Paul M. *Interval Therapy with Dimethyl Sulfoxide*. Ann NY Acad Sci Mar. 1967; 1(141):586-598.

Paulus E. *FDA advisory committee meeting: methotrexate; guidelines for the clinical evaluation of anti-inflammatory drugs; DMSO in scleroderma*. Arthritis & Rehumatism Oct. 1986; 10(29):1289-1290.

Pennsaid Monograph, Nuvo Research, 2010.

Penrod, D., Bacharach, B., Templeton, J. *Dimethyl Sulfoxide for Incisional Pain after Thoracotomy: Preliminary Report*. Annals New York Academy Sciences Mar. 15, 1967; vol. 141(1):493-495.

Potzz GE, Rampey JH, Bejamin F. *The effect of dimethyl sulfoxide (DMSO) on antibiotic sensitivity of a group of medically important microorganisms: preliminary report*. Ann NY Acad Sci. Mar. 15, 1967; 141(1):261-72.

Robertson et al. "*L-Arginine reduces neuronal damage after traumatic brain injury in the mouse*" Journal of Neurotrauma, vol. 17, No. 10, Oct. 2000, p. 945.

Kopek M, Pawlowska I, Szydlowska T. *Effects of dimethyl sulfoxide on tubercle bacilli resistant to INH*. Gruzlica. Aug. 1971; 39(8):738-41.

Rosenbaum WM, Rosenbaum EE, Jacob S. The use of dimethyl sulfoxide (DMSO) for the treatment of intractable pain in surgical patients. Surgery 1965: 58.

Roth SH, Shainouse JZ, Efficacy of Safety of a topical diclofenac solution (Pennsaid) in the treatment of primary osteoarthritis of the knee: a randomized, double-blind, controlled clinical trial. Arch Intern Med. Oct. 11, 2004;164(18):2017-23.

Scrubs, online encyclopedia article, accessed Mar. 10, 2010. http://en.wikipedia.org/wiki/Scrubs_(clothing).

Seibert F, Farrelly F, Shepherd C. *DMSO and other combatants against bacteria isolated from leukemia and cancer patients*. Ann NY Acad Sci Mar. 1967; 1(141):175-201.

Shainhouse JZ, Grierson L, Naseer Z, A long-term, open-label study to confirm the safety of topical diclofenac solution containing dimethyl sulfoxide in the treatment of the osteoarthritic knee, American Journal of Therapeutics 0(0) 2010.

Shaklee Health Network, "Methyl Sulfonyl Methane," [online], 2006 [retrieved on Dec. 16, 2010]. Retrieved from the internet: <URL:http://content.hbiondemand.com/shap/monoVMN.asp?objID=100028]: p. 1-4, especially p. 1, para 1 to p. 2, para 1.

Simon L, et. al. *Efficacy and Safety of Topical Diclofenac containing Dimethyl Sulfoxide (DMSO) compared with those of Topical Placebo, DMSO Vehicle and Oral Diclofenac for Knee Osteoarthritis*. Pain, 143(2009):238-245.

Smith G, Bertone AL, Kaeding C, et al. *Anti-Inflammatory effects of topically applied dimethyl sulphoxide gel on endotoxin-induced synovitis in horses*. Am J Vet Res Sep. 1998; 59(9):1149-52.

Steinberg, A. *The employment of DMSO as an anti-inflammatory agent and steroid transporter in diversified clinical diseases*. Ann NY Acad Sci 1967, 141(1):532-550.

Szydlowska T. In Vitro and In Vivo *Studies on the role of Dimethylsulfoxide (DMSO) in Resensibilization of Bacterial Strains Resistant to Antibiotics and Chemotherapeutic Agents*. Zbl. Bakt. Hyg., I. Abt. Orig. A 239, 270-274 (1977).

Szydlowska T, Pawlowska I. *Comparative Studies on the Influence of Dimethylsulfoxide (DMSO) on Reversion to Sensitivity to Isonicotinic Acid Hydrazide (INH) and Rifampicin (RMP) in Resistant Strains of Tubercle Bacilli*. Arch Immunol Ther Exp (Warsz). 1976; 24(4):575-77.

Szydlowska T, Pawlowska I. In vivo *studies on reversion to sensitivity of INH-resistant tubercle bacilli under the influence of dimethylsulfoxide (DMSO)*. Arch Immunol Ther Exp (Warsz). 1974; 22(4):559-61.

Szydlowska T. *Studies on the role of dimethylsulfoxide in resensibilization of antibiotic-resistant bacterial strains*. Arch Immunol Ther Exp (Warsz). 1972; 20(2):193-202.

Szydlowska T. *Studies on the role of dimethylsulfoxide in resensibilization of bacterial strains resistant to sulfonamides*. Arch Immunol Ther Exp (Warsz). 1972; 20(2):203-207.

Teigland MB, Saurino V. *Clinical Evaluation of Dimethyl Sulfoxide in Equine Applications*. Ann NY Acad Sci Mar. 1967; 141(1):471-7.

Tugwell PS, Wells GA, Shainhouse JZ. Equivalence study of a topical diclofenac solution (Pennsaid) compared with oral

(56) References Cited

OTHER PUBLICATIONS diclofenac in symptomatic treatment of osteoarthritis of the knee: a randomized, controlled trial. J Rheumatol. Oct. 2004; 31(10):1893-5.
Usha PR, Naidu MUR. *Randomized, double-blind, parallel, placebo-controlled study of oral glucosamine, methylsulfonylmethane and their combination in osteoarthritis*. Clin Drug Invest 2004; 24(6):353-63.
Vuopala U, et. al. *The Analgesic action of DMSO ointment in arthrosis*. Acta Rheum Scand 1971; 17(1):57-60.
Wierzbicki, Homocysteine and cardiovascular disease: a review of the evidence; Diabetes and Vascular Disease Research; Jun. 2007; pp. 143-149; vol. 4, Iss 2; The British Library.
Wiesinger, Heinrich "Arginine metabolism and the synthesis of nitric oxide in the nervous system," Progress in Neurobiology 64, 365-91, 2001.
Wood, DC, Wood, J. *Pharmacologic and Biochemical Considerations of Dimethyl Sulfoxide*. Ann NY Acad Sci Jan. 1975; 243:7-19.
Zuckner, J. Uddin, J., Gantner, G. *Local Application of Dimethyl Sulfoxide and DMSO Combined with Triamcinolone Acetonide in Rheumatoid Arthritis*. Ann NY Acad. Sci. Mar. 1967; 1(141):555-9.
Adam, JB, Summary of Biomedical Treatments for Autism, ARI Publication 40, Apr. 2007.
Additive Free MSM Methylsulfonylmethane. World Image Naturals™, Inc. 2005. Downloaded from http://www.worldimagenaturals.com/products/msm/index.php. pp. 1-6.
AloeCalm™ All-Natural and Organic Body Lotion. Lanique Botanicals™. Downloaded from http://www.acne-answers.org/products/aloe-calm.html on Jul. 5, 2010. pp. 1-5.
Andrews, Jennifer M.: "Determination of minimum inhibitory concentrations," Journal of Antimicrobial Chemotherapy (2001) 48, Suppl. Sl, 5-16.
Beilke, et al.: "Effects of dimethyl sulfoxide on the oxidative function of human neutrophils," (1987) Journal of Laboratory and Clinical Medicine 110:91-96.
Borodina, et al.: "Dimethylsulfone as a growth substrate for novel methylotrophic species of *Hyphomicrobium* and *Arthrobacter*," Arch Microbiol (2000) 173: 425-437.
Brandt, et al.: "Selective Affinity of Dimethyl Sulphoxide (DMSO) and 2-amino-4-phenylsulphonylbenzenesulphonamide (NSD 3004) for the Large Intestinal Mucosa of Mice," Acta pharmacol. Et toxicol. 1982, 51, 173-176.
Brown, Derek, F.J., et al.: "Guidelines for the laboratory diagnosis and susceptibility testing of methicillin-resistant *staphylococcus aureus* (MRSA)," Journal of Antimicrobial Chemotherapy (2005) 56, 1000-1018.
Cárdenas, et al., "Fructose-1,6-bisphosphate inhibits the expression of inducible nitric oxide synthase caused by oxygen-glucose deprivation through the inhibition of glutamate related in rat forebrain slices", Arch. of Pharmacol., vol. 362(3):208-121 (2000).
Dancer, S. J.: "The effect of antibiotics on methicillin-resistant *Staphylococcus aureus*," Journal of Antimicrobial Chemotherapy (2008) 61, 246-253.
Database WPI, Week 199604, Thomson Scientific.
de Lencastre, et al.: "Antibiotic resistant *Staphylococcus aureus*: a paradigm of adaptive power," Curr Opin Microbiol. Oct. 2007; 10(5): 428-435.
Gerhards & Gibian, "The Metabolism of Dimethyl Sulfoxide and Its Metabolic Effect in Man and Animals," Annals New York Academy of Sciences, pp. 65-76, Mar. 1967.
Gupta, Shyam Dr.: "New Delivery System for Topical Nutraceutical (Nutracosmetic) and Cosmeceutical Formulations," pp. 1-5, Business Briefing: Global Cosmetics Manufacturing 2004.
Horváth, et al.: "Toxicity of methylsulfonylmethane in rats," Food and Chemical Toxicology 40 (2002) 1459-1462.
How to Flush the Toxins out of Your Body from the Swine or H1N1 Flu Shot, downloaded from http://www.ehow.com/print/how_5625054_flush-swine-hn-flu-shot.html, on Aug. 18, 2010. pp. 1-3.

Rucker, et al.: "Studies on The Absorption, Excretion and Metabolism of Dimethylsulfoxide (DMSO) in Man," The Journal of Pharmacology and Experimental Therapeutics, 155:309-317. 1967.
Jacob & Herschler: "Introductory Remarks: Dimethyl Sulfoxide After Twenty Years," Annals New York Academy of Sciences, Jun. 1983.
Khazina et al., Tuberculostatic effect of the combined use of isoniazid and streptomycin with 5-fluorouracil in vitro, Problemy Tuberkuleza, Medicina, Moscow, Russia, vol. 58 (1): 63-66 (1980).
Layman, et al.: "The Absorption, Metabolism and Excretion of Dimethyl Sulfoxide by Rhesus Monkeys," Life Sciences, vol. 37, pp. 2431-2437, 1985.
Lee, et al.: "Evaluation of Genotoxicity on Plant-Derived Dietary Sulfar," J. Microbiol. Biotechnol. (2006), 16(5), 817-820.
Life Extension Magazine, Sep. 1999 "The Multi-Purpose Compound MSM".
Lu, et al.: "A Mouse Model for the Evaluation of Pathogenesis and Immunity to Influenza A (H5N1) Viruses Isolated from Humans," Journal of Virology, Jul. 1999, p. 5903-5911.
Magnuson, et al.: "Oral developmental toxicity study of methylsulfonylmethane in rats," Food and Chemical Toxicology 45 (2007) 977-984.
Magnuson, et al.: "Pharmacokinetics and Distribution of [$^{35}$S]Methylsulfonylmethane following Oral Administration to Rats," J. Agric. Food Chem. 2007, 55, 1033-1038.
Methylsulfonylmethane—Wikipedia, the free encyclopedia. Download from http://en.wikipedia.org/wiki/Methylsulfonylmethane, on Jul. 5, 2010. pp. 1-5.
MSM—MethylsulfonylMethane. Downloaded from http://pages.prodigy.net/naturedoctor/msm.html on Jul. 5, 2010. pp. 1-6.
Pratt, et al.: "A Study of the Absorption of OptiMSM (Methylsulfonylmethane) in Horses," Proceedings of the 17th Equine Nutrition and Physiology Society, 2001.
Ramirez, et al., DMSO in the Treatment of Mental Patients, Annals of the NY Acad. of Sci., vol. 141: 655-667 (1967).
Rao et al., In vitro induction of nitric oxide by fructose-1,6-diphosphate in the cardiovascular system of rats, Mol. Cell. Biochem. vol. 185:171-175 (1998).
Shanmugam, et al.: "The Effect of Methylsulfonylmethane on Hair Growth Promotion of Magnesium Ascorbyl Phosphate for the Treatment of Alopecia," Biomolecules & Therapeutics, 17(3), 241-248 (2009). ISSN 1976-9148.
Stürenburg, Enno: "Rapid detection of methicillin-resistant *Staphylococcus aureus* directly from clinical samples: methods, effectiveness and cost considerations," GMS German Medical Science 2009, vol. 7, ISSN 1612-3174. pp. 1-19.
Sulfur—MSM—methyl sulfonyl methane—Natural Health Site. A Basic Essential Nutrient Needed Now, More than Ever Before. Downloaded from http://www.all-natural.com/msm.html on Aug. 11, 2010. pp. 1-7.
Szmant, Harry H., "Physical Properties of Dimethyl Sulfoxide and Its Function in Biological Systems," Annals New York Academy of Sciences, pp. 20-23, Jan. 1975.
Tiews, et al.: "Metabolism and Excretion of Dimethyl Sulfoxide in Cows and Calves After Topical and Parenteral Application," Annals New York Academy of Sciences, pp. 139-150. Jan. 1975.
Vignes, Robert P., Ph.D: "Dimethyl Sulfoxide (DMSO): A Superior Solvent," Semiconductor Safety Association, Annual Meeting Apr. 25-28, 2000, Arlington, VA. pp. 1-47.
Williams, et al.: "Metabolism of Dimethyl Sulfide, Dimethyl Sulfoxide, and Dimethyl Sulfone in the Rabbit," Archives of Biochemistry and Biophysics 117, 84-87 (1966).
Windrum, et al.: "Variation in dimethyl sulfoxide use in stem cell transplantation: a survey of EBMT centres," Bone Marrow Transplantation (2005) 36, 601-603.
Wong, et al.: "Absorption, Excretion, and Biotransformation of Dimethyl Sulfoxide in Man and Minature Pigs After Topical Applicaton As an 80% Gel," The Journal of Investigative Dermatology, vol. 56, No. 1, 1971.
Yang, TR, Gas Separation by Adsorption Process, Imperial College Press, 1987 pp. 11-12.

(56) References Cited

OTHER PUBLICATIONS

Zhang, et al.: "Assessment of methysulfonylmethane as a permeability enhancer for regional EDTA chelation therapy," infoma healthcare, Drug Delivery, 2009, 16(5): 243-248.
Jacob, Web page entitled DMSO Dimethyl Sulfoxide, www.dmso.org; retrieved from the internet on Mar. 25, 2010.
Jacob, Web page entitled Dr. Jacob's Quality Assurance, www.Jacoblab.com; as published on the Internet on Sep. 8, 2004.
Jacob, Web page Dr. Jacob's Quality Assurance, Natural Healthcare Solutions; www.jacoblab.com; retrieved from Internet on Mar. 25, 2010.
Ruslami et al., Pharmacokinetics and Tolerability of a Higher Rifampin Dose Versus the Standard Dose in Pulmonary Tuberculosis Patients, Antimicrobial Agents and Chemotherapy, vol. 51(7):2546-2551 (2007).
Simon et al.: "Efficacy and safety of a topical diclofenac solution compared with topical placebo, vehicle, oral diclofenac and oral/topical combination in the symptomatic treatment of osteoarthritis of the knee," Arthritis & Rheumatism, vol. 58, No. 9, Suppl. S, Sep. 2008 (Sep. 2008), p. S483, & 72nd Annual Scientific Meeting of the American College-of-Rheumatology/43rd Annual Scientific Meeting, San Francisco, CA, USA, Oct. 24-29, 2008 ISSN: 0004-3591.

\* cited by examiner

DIMETHYL SULFOXIDE (DMSO) AND METHYLSULFONYLMETHANE (MSM) FORMULATIONS TO TREAT OSTEOARTHRITIS

RELATED APPLICATIONS

This application is the U.S. National Phase application under 35 U.S.C. §371 of International Application PCT/US2010/054870, filed on Oct. 29, 2010, which claims the benefit of U.S. Provisional Patent Application Nos. 61/256,935, filed on Oct. 30, 2009; and 61/319,203, filed Mar. 30, 2010, the disclosure of each of which is expressly incorporated by reference herein.

BACKGROUND

Field of the Invention

Embodiments of the invention relate generally to formulations comprising dimethyl sulfoxide (DMSO) and/or methylsulfonylmethane (MSM) and the use of those compounds for the treatment of arthritis (such as osteoarthritis) and other conditions. Solid formulations comprising DMSO, alone or in combination with MSM, are provided in several embodiments.

Description of the Related Art

Cartilage is a protein matrix which functions to lubricate and cushion the joints. Osteoarthritis, or degenerative arthritis, refers to a class of diseases and mechanical abnormalities that result in degradation of joints, structurally and therefore, functionally. The articular cartilage of joints and the juxtaposed subchondral bone (e.g., the ends of the bone) are frequently affected.

Clinically, osteoarthritis may present with symptoms such as joint pain or minor tenderness of load bearing joints. Symptoms range from this level of "everyday aches and pains" to severe sensitivity of joints, stiffness, inflammation, creaking, and locking of joints.

Osteoarthritis is the most common form of arthritis in the United States, affecting nearly 27 million people, and is the leading cause of chronic disability. Osteoarthritis is linked to approximately 25% of visits to primary care physicians, and about 50% of non-steroidal anti-inflammatory prescriptions. Thus, in its various stages, osteoarthritis accounts for an enormous burden on those who suffer from the disease, their family and caretakers, as well as the medical community.

Severe cases of osteoarthritis may require surgery to replace joints, remove bone fragments, reposition and/or fuse bones to increase stability and reduce pain. However, these surgeries are costly, are associated with long recovery times, and in some cases do not lead to significant alleviation of symptoms.

Dimethyl sulfoxide (DMSO; $(CH_3)_2(SO)$) is a polar, aprotic solvent widely used as a solvent. It is frequently used in various chemical and biological reactions and as a cryoprotectant for cell storage. The strong unpleasant odor of DMSO, along with several undesired side effects, have adversely impacted the use of DMSO in medical applications.

Methylsulfonylmethane (MSM; $(CH_3)_2SO_2$)), also known as dimethyl sulfone, is an organosulfur compound that is a metabolite of DMSO and certain sulfur-containing amino acids. MSM has been marketed primarily as a dietary supplement.

SUMMARY

The etiology of osteoarthritis is varied, and includes hereditary, developmental, metabolic, and mechanical aspects that may lead to loss of cartilage. Ironically, the responses generated by the body (e.g., immune and regrowth processes) may accelerate damage to the cartilage. For example, when bone surfaces lose cartilage, subchondral bone may be exposed, damaged, and regrown. However, regrowth may lead to excessive proliferation of dense bone in central areas of cartilage loss, further exacerbating the cartilage loss. As a result, a person suffering from progressive osteoarthritis may experience increasing pain upon weight bearing, including walking and standing. Additionally, the decreased movement because of the pain may cause regional muscles to atrophy and reduce tension on ligaments, further compromising the functionality of the joint.

Several options for therapy are available currently for those afflicted with osteoarthritis. Paracetamol (Tylenol®/acetaminophen) is commonly used to treat osteoarthritis pain and has demonstrated roughly equivalent benefit to ibuprofen. However, doses demonstrating effective pain relief (~4 g/day) have been associated with alterations in liver function as well as gastrointestinal bleeding or renal damage when used chronically.

Non-steroidal anti-inflammatory (NSAID) drugs may be prescribed for more severe cases of osteoarthritis. This class of drugs acts by inhibiting the formation of prostaglandins and may reduce both the pain and inflammation associated with osteoarthritis. These drugs, however, are also associated with adverse events including increased gastrointestinal bleeding, stomach upset, cramping, diarrhea, and peptic ulcer. Some of these drugs, namely the cyclooxygenase-2 inhibitors, have been withdrawn from the market due to their elevated risk for cardiovascular disease. Several NSAIDS are available for topical use, though the therapeutic effect is generally minimal and short lived.

Oral corticosteroids carry a high rate of adverse side effects and produce limited symptomatic improvement, and therefore are not typically recommended for osteoarthritis treatment. Injections of corticosteroids into the intra-articular space may provide acute (e.g., several weeks) relief of pain, but do not generally offer a long term therapeutic effect.

Thus, there remains a need in the art for an effective treatment for osteoarthritis, particularly one that addresses both the chronic condition of osteoarthritis as well as the acute symptoms associated with the illness. Accordingly, in several embodiments, formulations comprising MSM and DMSO, individually or combined, are provided for either oral or topical use, either alone or in combination, to provide efficacious relief of both chronic and acute symptoms of osteoarthritis, while inducing minimal, reduced, or no, side effects.

In several embodiments, formulations comprising DMSO and MSM, individually or combined, are formulated as solids. A solid form of DMSO, alone or in combination with MSM is particularly surprising and beneficial because, in some embodiments, the solid form is associated with less odor than the liquid form. In several embodiments, the solid form stays solid at room temperature (e.g., about 20° C.-23° C.). In other embodiments, the solid form stays solid at temperatures up to 30° C., 45° C., 60° C., 75° C., 100° C., or higher. In some embodiments, the solid form does not crystallize and/or lose its texture at temperatures below room temperature, 25° C., 15° C., 10° C., 5° C., or lower. In several embodiments, the solid form maintains its chemical stability and/or integrity (e.g., phase integrity) at a wide range of temperatures, including but not limited to ranges between about 0° C. to about 100° C., about 5° C. to about 50° C., about 10° C. to about 40° C., about 20° C. and about 30° C., and overlapping ranges thereof. In several embodiments, the solid form maintains a similar consistency, e.g., maintains one or more of a hardness, firmness, density, texture, and/or viscosity that is at least 75%, 85%, 95% or 100% the same, over a range of temperatures from about 0° C. to about 100° C., about 5° C. to about 50° C., about 10° C. to about 40° C., about 20° C. and about 30° C., and overlapping ranges thereof. In several embodiments, the addition of a coating to the solid form and/or a stabilizer increases the stability temperature stability range by at least 10%, 25%, 50% or more. In one embodiment, the solid form maintains its chemical stability and/or integrity (e.g., phase integrity) in a range from about 10° C. to about 40° C. without a coating and about 0° C. to about 50° C. with a coating. Coatings include, but are not limited to, vegetable-based coatings, biopolymers, colloidal particles, multilayer emulsions, colloidosomes, or combinations thereof.

In several embodiments, solid forms of DMSO, alone or in combination with MSM, are provided in the form of a capsule. In one embodiment, the use of solidified DMSO reduces the odor typically associated with DMSO. In another embodiment, the use of solidified DMSO reduces the physiological side effects typically associated with DMSO. In some embodiments, the formulations are consumed orally to treat osteoarthritis, while in some other embodiments, the formulations are applied topically. In still other embodiments, both oral and topical formulations are used. In several other embodiments, formulations comprising DMSO and MSM, individually or combined, are formulated as liquids.

As used herein, the phrase "symptoms of osteoarthritis" shall be given its ordinary meaning and shall include, but not be limited to, one or more of the following: cartilage degeneration, degeneration of subchondral bone, joint pain, tenderness, stiffness, creaking, locking of joints, inflammation, structural changes in the joint, swelling, diminished grip strength, bony enlargement, diminished range of motion, osteophyte (or spur) formation, and synovial irritation. Symptoms of osteoarthritis can occur, for example, in the knee, toe, thumb, finger, ankle, spine, hip, shoulder or other joint.

In several embodiments, formulations comprising MSM, DMSO and/or a combination of MSM and DMSO, alone or with other colors, flavorings, additives, fillers, carriers, excipients, and/or therapeutics are used to prevent and/or treat osteoarthritis and/or symptoms thereof, arthritis and/or symptoms thereof, inflammation, joint pain, and/or structural changes of the joint.

In several embodiments, formulations comprising MSM, DMSO and/or a combination of MSM and DMSO, alone or with other carriers, flavorings, additives, fillers, carriers, excipients, and/or therapeutics are used to prevent and/or treat the following conditions that are unrelated to an osteoarthritic etiology: tissue degeneration, pain (e.g., joint pain), and/or inflammation.

Due to its physical properties, DMSO exists as a liquid at room temperature, and is therefore typically utilized as a liquid. However, there is a long felt and as yet unmet need for a solid form of DMSO at room temperature. For example, a solid form of DMSO is particularly advantageous because, in some embodiments, it can be provided as a pill, tablet or capsule, is suitable for concentrated dosages, and exhibits reduced side effects as compared to a liquid form (e.g., less irritation, sensitivities, gastrointestinal effects, etc.). In several embodiments, solid forms offer controlled release in the body, and in some embodiments, are more slowly released and/or more effectively absorbed. In one embodiment, a solid form that dissolves in a desired area (e.g., small intestine) is provided, thereby offering enhanced bioavailability based on targeted delivery. Further, solid forms of DMSO exhibit reduced or no odor as compared to the liquid form in some embodiments. Thus, several embodiments of the present invention provide a formulation comprising DMSO that is solid at room temperature, and methods of making same.

In several embodiments, formulations comprising DMSO and MSM (and/or a compound related to MSM) exhibit reduced odor than formulations comprising DMSO alone. Formulations in liquid, gel, solid, and/or gaseous forms exhibit reduced odor when DMSO is combined with MSM (and/or a compound related to MSM) in some embodiments.

In several embodiments, the invention comprises an oral and topical system for improving the symptoms of arthritis (e.g., osteoarthritis), including, but not limited to, pain, osteophytes, stiffness, grip strength, limited range of motion, tissue enlargement in joints, inflammation (specific to a joint or localized to a general region of the body), swollen joints, joint deformity, and combinations thereof. In one embodiment, the system comprises a first formulation comprising DMSO and MSM, wherein said first formulation is suitable for oral administration. In some embodiments, the first formulation comprises about 300 mg to about 750 mg MSM and about 10 mg to about 50 mg DMSO. In some embodiments, the first formulation comprises about 300 mg to about 700 mg MSM and about 10 mg to about 50 mg DMSO. The second formulation comprises DMSO and MSM, and is suitable for topical administration. In some embodiments, the second formulation comprises between about 100 mg and about 1500 mg MSM and between about 500 mg and about 5000 mg DMSO, depending on the volume applied. The second formulation, in some embodiments, comprises about 900 mg to about 1200 mg MSM and about 3000 mg to about 5000 mg DMSO. In some embodiments, the second formulation comprises about 10% to about 15% MSM and about 40% to about 70% DMSO, or higher (e.g., up to 90% or more DMSO).

In one embodiment, the first formulation (e.g., oral) comprises 650 mg MSM and 15 mg DMSO and the second formulation (e.g., topical) comprises 10% MSM and 50% DMSO. In one embodiment, the first formulation comprises 500 mg MSM and 15 mg DMSO and the second formulation comprises 917 mg MSM and 4585 mg DMSO. In one embodiment, an oral formulation comprises 400-600 mg MSM and 10-20 mg DMSO and a topical formulation comprises 800-1000 mg MSM and 3500-5000 mg DMSO.

In one embodiment, the first formulation comprises about 900 mg to about 2100 mg MSM and about 30 mg to about 150 mg DMSO and the second formulation comprises about 10% to about 15% MSM, and about 50% to about 90% DMSO. In one embodiment, the first formulation comprises about 900 mg to about 2100 mg MSM and about 30 mg to about 150 mg DMSO and the second formulation comprises about 2700 mg to about 3600 mg MSM, and about 9000 mg to about 15,000 mg DMSO.

In one embodiment, the first formulation comprises about 1500 mg MSM and about 45 mg DMSO and the second formulation comprises about 10% MSM and about 50% DMSO. In one embodiment, the first formulation comprises about 1500 mg MSM and about 45 mg DMSO and the second formulation comprises about 2751 mg MSM and about 10,800 mg DMSO.

In one embodiment, the first formulation comprises about 60-99% MSM, and about 0.1-3% DMSO and the second formulation comprises about 10-15% MSM, and about 50-70% DMSO, or higher (e.g., up to 90% or more DMSO).

In one embodiment, the first formulation comprises about 60-70% MSM and about 0.1-3% DMSO and the second formulation comprises about 10%-15% MSM and about 40%-90% (e.g., 50%-70%) DMSO.

In one embodiment, the first formulation comprises about 0.045 g/day DMSO and about 1.85 g/day MSM and the second formulation comprises about 50%-70% DMSO and about 10%-15% MSM. In one embodiment, an oral formulation comprises about 0.045 g/day DMSO and about 1.85 g/day MSM and a topical formulation comprises about 40%-90% DMSO and about 10%-15% MSM.

In several embodiments herein, only the first formulation (e.g., oral) is used (alone or combined with other compounds). In other embodiments, only the second formulation (e.g., topical) is used (alone or combined with other compounds). In yet other embodiments, a dual treatment approach is employed. In some embodiments, the dual treatment approach comprises an oral and topical therapy comprising DMSO, MSM and one or more additional compounds.

In one embodiment, the therapeutic system is suitable for treating a subject, and is administered (or is suitable for administration) in the following doses: the first formulation comprises about 10-30 mg MSM per kg body weight of the subject and about 0.1-1 mg DMSO per kg body weight and the second formulation comprises about 30-50 mg MSM per kg body weight and about 125-175 mg DMSO per kg body weight. In one embodiment, the second formulation comprises about 30-70 mg MSM per kg body weight and about 125-225 mg DMSO per kg body weight In one embodiment, the first formulation and/or the second formulation are administered (or are suitable for administration) at least once, twice or thrice daily.

In several embodiments, the MSM reduces an odor or other side-effect of the DMSO. In some embodiments, MSM reduces dermal irritation that may be caused by administration of DMSO. In some embodiments, DMSO reduces a side-effect of the MSM. In some embodiments, DMSO enhances the efficacy of the MSM. In some embodiments, the enhanced efficacy of the MSM is due to the DMSO in the oral formulation. In some embodiments, DMSO in the oral formulation reduces the amount of MSM that is required to achieve a given therapeutic result. MSM used according to any of the embodiments provided herein may be isolated, purified or processed. MSM that has been granted a GRAS (Generally Recognized As Safe) designation is used for several embodiments described herein.

In some embodiments, the first formulation is in a capsule, tablet, oral suspension, liquid, inhalant, and/or effervescent form, wherein said forms are optionally coated and/or flavored. The second formulation, according to some embodiments, is in a gel, cream, serum, liquid, spray, ointment, and/or patch form. Heat or cold therapy may be additionally provided in conjunction with the second formulation.

In several embodiments, the first oral formulation treats the chronic symptoms of osteoarthritis and/or generalized pain and/or injury and the second topical formulation treats the acute symptoms of osteoarthritis and/or localized pain and/or injury. The first and/or the second formulations are optionally provided in time-released formulations.

In one embodiment, the invention comprises the use of the formulations described herein in the preparation of a medicament for the treatment of osteoarthritis and/or symptoms of osteoarthritis. In one embodiment, the invention comprises a kit comprising one or more formulations according to any one of the preceding claims with instructions to administer the first formulation orally 1-4 times daily and/or instructions to administer the second formulation topically 1-4 times daily. In one embodiment, the instructions instruct the administration of the first formulation orally 3 times daily. The instructions may also instruct administration of the second formulation topically 1-4 times daily for up to two weeks. In one embodiment, the instructions instruct the administration of the second formulation topically 3 times daily for up to two weeks.

In several embodiments, the invention comprises a method for treating the symptoms of arthritis (e.g., osteoarthritis). Symptoms that are treated in some embodiments include one or more of pain, osteophytes, stiffness, grip strength, limited range of motion, tissue enlargement in joints, swollen joints, and joint deformity. In some embodiments, the invention comprises a method for treating the symptoms other types of arthritis, such as, for example, adult onset rheumatoid arthritis. In some embodiments, the invention is used to treat and/or improve the symptoms of juvenile rheumatoid arthritis. In one embodiment, the method comprises providing the first and second formulation as disclosed herein, orally administering or instructing oral administration of the first formulation to a subject 1-4 times daily; and topically administering or instructing topical administration of the second formulation to said subject 1-4 times daily.

In several embodiments of the invention, a topical formulation for improving the symptoms of osteoarthritis is provided. In one embodiment, the formulation comprises DMSO in an amount between about 2000 mg to about 5000 mg DMSO per dose (e.g., a 5 mL dose) and MSM in an amount between about 300 mg to about 1200 mg MSM per dose (e.g., a 5 mL dose). In one embodiment, the formulation comprises DMSO in an amount between about 3000 mg to about 5000 mg DMSO per dose and MSM in an amount between about 900 mg to about 1200 mg MSM per dose. In one embodiment, the DMSO and MSM are suitable for topical administration to a subject to improve the symptoms of osteoarthritis. In one embodiment, the DMSO and MSM are suitable for topical administration to a subject to treat one or more of joint disorders, inflammation, degeneration, and/or pain. Optionally, an oral formulation comprises about 300 mg to about 700 mg MSM and about 10 mg to about 50 mg DMSO per dose is provided.

In one embodiment, MSM is configured to act as a lubricant to reduce irritation associated with topical application of DMSO. In one embodiment, MSM reduces the odor associated with topical application of DMSO.

In one embodiment, the invention comprises a method of reducing the amount oral DMSO to achieve a therapeutic effect comprising: providing the oral or topical formulation as described herein to reduce the amount of DMSO needed to achieve a therapeutic effect, thereby reducing the side effects of DMSO.

In several embodiments, the invention comprises an oral formulation for improving the symptoms of arthritis (e.g., osteoarthritis). In one embodiment, the formulation comprises DMSO and at least one second compound in a solid form that is encapsulated in a capsule or other encapsulation format. In one embodiment, the capsule delivers said DMSO and at least one second compound in a time-released manner. In some embodiments, the oral formulation is analgesic and anti-inflammatory. The second compound reduces an odor associated with DMSO and reduces one or more side effects associated with DMSO. In one embodiment, the second compound is MSM, urea, a sulfur-binding agent, or combinations thereof. In one embodiment, the second compound comprises a nutrient (e.g., an amino acid). In one embodiment, the second compound comprises a carbonyl group attached to two organic amine residues. In one embodiment, the second compound includes carbamide peroxide, allantoin, and hydantoin, biurets, amides, carbamates, diimides, carbodiimides, thiocarbamides, or combinations thereof. Preferably, one or more of MSM, urea and/or a sulfur-binding compound are used, although other compounds are provided in several embodiments to reduce an odor or side-effect of DMSO.

In one embodiment, the encapsulated oral formulation is provided in a dosage of about 1 gram or less. In one embodiment, the formulation is suitable for administration 1-4 times per day with or without food. In some embodiments, the synergistic effects of DMSO and MSM do not require the formulation to be ingested with food. In several embodiments, the use of MSM permits higher concentrations of DMSO to be used and tolerated, by for example, reducing the side-effects of DMSO and/or reducing the odor associated with DMSO. In one embodiment, the use of MSM in amounts greater than 800 mg (e.g., in a single or daily dose) increase the tolerability of DMSO in amounts greater than 200 mg (e.g., in a single or daily dose).

In several embodiments of the invention, a formulation comprising DMSO in a solid form is provided. In some embodiments, the DMSO is in a solid phase at room temperature. The DMSO in solid formulation is suitable for the treatment of several disorders, including arthritis (e.g., osteoarthritis, rheumatoid arthritis), and other disorders that would benefit from DMSO treatment (e.g., osteophyte formation). In some embodiments, the solid formulation is used for the treatment of inflammation, pain, or a combination thereof. In several embodiments, DMSO and MSM are combined to form a solid, wherein the solid remains a solid at room temperature. The solid formulation includes, but is not limited to, a capsule, a gel-cap, a tablet, an oral suspension, a powder, an effervescent, or combinations thereof. A coating is provided in some embodiments. The coating provides sustained-release, sustained-action, extended-release, controlled-release, or continuous-release of the formulation according to several embodiments. In some embodiments, the coating further provides a flavorant. In one embodiment, DMSO is between about 0.01% to about 10% by weight of the formulation. In another embodiment, DMSO is between about 45% to about 55% by weight of the formulation. In one embodiment, the formulation is provided in a capsule comprising about 100 mg to about 1000 mg of said DMSO, wherein said capsule is suitable for delivery 1-4 times daily.

In several embodiments, the invention comprises a method for producing DMSO in a form that is solid at room temperature. In one embodiment, the method comprises providing DMSO in a liquid form, combining said liquid DMSO with hydrogen peroxide, heating the liquid DMSO and the hydrogen peroxide to obtain a combination of DMSO and MSM, cooling the DMSO and MSM combination into a solid formulation, wherein said solid formulation is solid at room temperature. Flaking, prilling and/or freezing is performed according to some embodiments.

DETAILED DESCRIPTION

Figure 1:
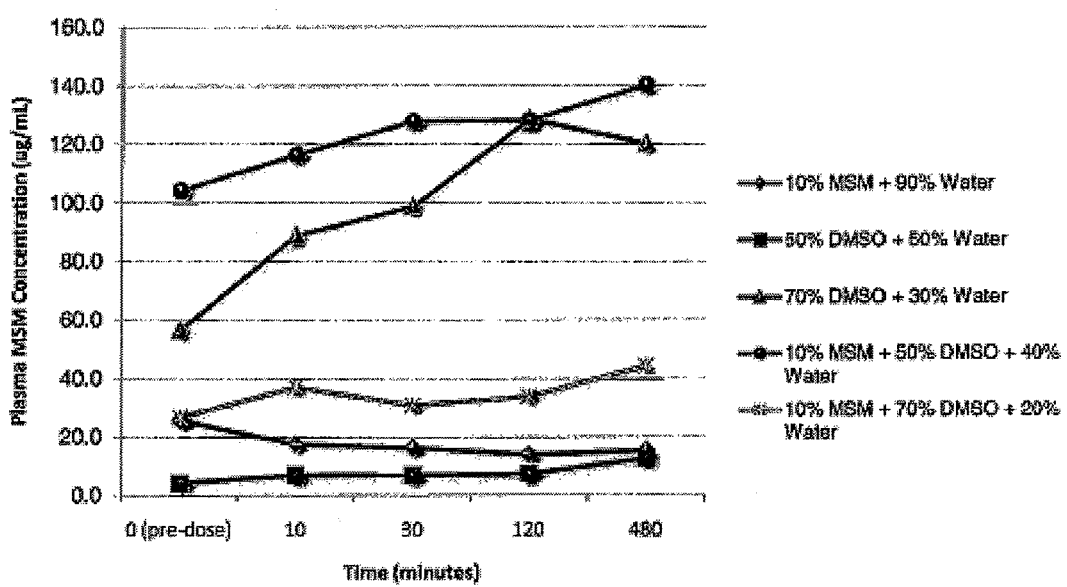
FIG. 1 depicts plasma concentrations of MSM after a 5 minute topical exposure to 10% MSM and varied concentrations of DMSO.

The invention, in some embodiments, comprises a formulation comprising DMSO and MSM, individually or combined, to treat the chronic effects of osteoarthritis as well the acute symptoms associated with osteoarthritis. In several embodiments, the invention comprises a therapeutic system comprising DMSO and MSM, individually or combined, to treat generalized pervasive pain via an oral formulation and localized pain via a topical formulation. In one embodiment, topical formulations of DMSO and/or MSM are also effective for generalized pain. In several embodiments, formulations comprising DMSO and MSM, individually or combined, are multifunctional in that the formulations not only treat the symptoms of an illness (such as osteoarthritis), but also confer unrelated benefits (e.g., improvements in skin and other aesthetic benefits, cardiovascular health, neurological health, immunity, vision, etc.).

As discussed herein, in several embodiments, there is provided an oral and topical dual formulation system for improving the symptoms of arthritis (including but not limited to osteoarthritis), the system comprising a first formulation comprising DMSO and a sulfur-binding and/or sulfur-based agent (including but not limited to MSM), wherein the first formulation is suitable for oral administration, wherein the first formulation comprises about 300 mg to about 750 mg MSM (or other agent) and about 10 mg to about 50 mg DMSO (e.g., about 650 mg MSM, or other agent, and about 15 mg DMSO) and a second formulation comprising DMSO and MSM (or other agent), wherein the second formulation is suitable for topical administration, wherein the second formulation comprises about 10% to about 15% MSM (or other agent) about 40% to about 70% DMSO, or higher (e.g., about 10% MSM, or other agent, and about 50% DMSO).

Unless stated otherwise, percentages of MSM, DMSO or other compounds provided herein are provided as % by weight.

In one embodiment, a dual formulation system comprising an oral dosage of 500 mg MSM and 15 mg DMSO together with a topical dosage of 50% DMSO and 10% MSM is provided. The oral dosage may be in the form of a tablet, capsule, powder, liquid, oral suspension, effervescent, or any other form suitable for oral delivery. The topical dosage may be in the form of a spray, gel, cream, lotion, patch, or any other form suitable for topical delivery. In some embodiments, the formulation is administered intravenously or via inhalation in addition to, or instead of, oral administration.

In several embodiments, the combined use of MSM reduces or eliminates the odor normally associated with DMSO. In some embodiments, the use of solid DMSO reduces or eliminates the odor normally associated with DMSO. The odor reduction is surprising, and beneficial in several embodiments because practitioners have avoided using DMSO in high concentrations (or in any amount) because of its unpleasant odor.

In some embodiments, the invention comprises an oral formulation of DMSO and MSM. In other embodiments, the invention comprises a topical formulation of DMSO and MSM. According to one embodiment, the topical formulation is particularly advantageous because MSM reduces or eliminates the skin irritation that can result from that topical application of DMSO. For example, in some embodiments, MSM acts as a lubricant and/or barrier that shields the skin from DMSO while still permitting penetration. In one embodiment, topical DMSO in concentrations greater than 25% (e.g., 50%, 70%, or more) are tolerated because of the presence of MSM. In one embodiment, the presence of MSM reduces the formation of rash, redness, dryness of skin, itching, and/or combinations thereof. In one embodiment, MSM reduces the occurrence, probability or symptoms associated with a generalized allergic reaction to DMSO, including heart arrhythmias and breathing difficulties. Because higher concentrations of DMSO can be administered topically in certain embodiments, the oral dose of DMSO can be reduced, thereby reducing the gastrointestinal side effects that can result from the topical administration of DMSO.

In several embodiments, the amount of DMSO is reduced when combined with MSM because of additive or synergistic effects between DMSO and MSM. In several embodiments, the amount of MSM is reduced when combined with DMSO because of additive or synergistic effects between DMSO and MSM. In several embodiments, MSM is provided in solution in a concentration of less than about 15%. In some embodiments, oral doses of MSM of less than about 2 grams per day are administered (e.g., 1 g, 1.5 g, 1.75 g and 1.85 g) to reduce gastrointestinal side effects in certain applications. In several embodiments, DMSO increases the penetration of MSM into tissue (e.g., skin).

In another embodiment, a formulation comprises, consists or consists essentially of an oral dosage (e.g., a solid form) of about 200 mg to about 2000 mg MSM and about 1 mg to about 100 mg DMSO together with a topical dosage of about 5% to about 90% DMSO and about 1% to about 50% MSM. In some such embodiments, MSM in the oral dosage ranges from about 200 to 500 mg, 500 to 800 mg, 800 to 1100 mg, 1100 to 1400 mg, 1400 to 1700 mg, 1700 to 2000 mg, and overlapping ranges thereof. In some such embodiments, DMSO in the oral dosage ranges from about 10 to 30 mg, 30 to 50 mg, 50 to 70 mg, 70 to 90 mg, 80 to 100 mg, and overlapping ranges thereof. In one embodiment, the invention comprises, consists or consists essentially of about 200 mg to about 2000 mg MSM and about 1 mg to about 100 mg DMSO, e.g., 400-600 mg MSM and 10-20 mg DMSO, 500 mg MSM and 15 mg DMSO, or 650 mg MSM and 15 mg DMSO.

In several embodiments, the invention comprises an oral formulation (e.g., a solid form) comprising a ratio of MSM to DMSO of 33:1, and optionally, a topical formulation comprising a ratio of MSM to DMSO of 1:5. In other embodiments, the invention comprises an oral formulation having a ratio of MSM to DMSO of 30-50:1, and optionally, a topical formulation having a ratio of MSM to DMSO of 1:2-10. In yet other embodiments, the invention comprises an oral formulation having a ratio of MSM to DMSO of 25-35:1, and optionally, a topical formulation having a ratio of MSM to DMSO of 1:3-7. The ratio of MSM to DMSO in several embodiments is surprisingly advantageous because the MSM synergistically improves the efficacy of DMSO. Thus, DMSO, which may have side effects when administered at certain concentrations, may be provided at lower concentrations to offer the same or better therapeutic efficacy. As discussed herein, the presence of MSM in certain embodiments functions as an emollient. In some embodiments, MSM reduces the odor normally associated with DMSO.

In some embodiments, the invention comprises a method of managing the symptoms of osteoarthritis by administering an oral dosage of MSM and DMSO daily for at least 1 month, together with a topical dosage of DMSO and MSM daily for about two weeks. Certain embodiments are particularly advantageous because they permit fast-acting symptom relief with the topical dosage, while allowing the oral dosage to gradually provide long-term relief. In some embodiments, relief is provided for extended periods of time, e.g., a week or more, several weeks, about a month, two months or more. At the point when the oral dosage becomes effective, patients can discontinue repetitive use of the topical formulation, thus reducing the risk of skin irritation and/or localized bioaccumulation. In still other embodiments, once the oral dosage has reduced pain and/or symptoms, the topical formulation is not necessary. In some embodiments, the dosage of the oral or the topical formulations is adjusted to personalize the therapy for a particular individual. For example, if an individual normally has limited chronic symptoms, but severe acute symptoms, a lower dose oral formulation with a higher dose topical formulation may be used. In other embodiments, an individual with more severe chronic symptoms, and few acute symptomatic episodes may benefit from a higher dose oral formulation and a less concentrated topical formulation. Thus, a dual formulation comprising both oral and topical routes of administration are surprisingly advantageous in several embodiments.

Oral formulations comprising MSM and DMSO, individually or combined, are administered multiple times per day in certain embodiments. In some embodiments, dosing occurs two, three, four or more times daily, depending on the severity of the osteoarthritis symptoms. In other embodiments, oral formulations are taken once per day. Topical formulations, in certain embodiments, are used multiple times daily, for example two, three, four or more times. In other embodiments, topical formulations are used only for treatment of acute exacerbation of symptoms. In some embodiments, oral formulations are used in conjunction with topical formulations, while in other embodiments, only oral formulations are administered.

In certain embodiments, formulations comprising MSM and DMSO, individually or combined, (oral, topical, or combinations thereof) are efficacious in ameliorating one or more symptoms of osteoarthritis. In some embodiments, formulations comprising MSM and DMSO, individually or combined, reduce or prevent pain or stiffness in one or more joints during periods of rest. In some embodiments, formulations comprising MSM and DMSO, individually or combined, reduce or prevent pain or stiffness in one or more joints during periods of light or moderate activity. In still other embodiments, formulations comprising MSM and DMSO, individually or combined, reduce or prevent pain or stiffness in one or more joints during periods of strenuous activity. In several embodiments, formulations comprising MSM and DMSO, individually or combined, reduce pain, stiffness and/or inflammation at rest, during activity, and/or post-activity.

In several embodiments, the combination of DMSO and MSM in a single formulation results in a synergistic effect, thereby lowering the concentration of DMSO, MSM, or both DMSO and MSM needed to effectively reduce one or more symptoms of osteoarthritis. Toxicology studies have established that DMSO can be chronically administered at 5 g/kg daily without any serious adverse effects. In certain embodiments, the dosage of oral DMSO ranges from about 0.003 to 0.06 g per day. In some embodiments, the dosage of oral DMSO is about 0.045 g per day. Assuming an average of 50 kg per subject, these dosages equate to a range of about 0.00006 to about 0.0012 g/Kg daily (0.0012 to 0.024% of the dose given in the toxicology studies without serious adverse effect).

Oral toxicity of MSM has been previously determined through standard methods in rats. The $LD_{50}$ value was approximately 17 g/kg, which corresponds to an oral dose of 2.6 pounds per day for a 150 pound human. In certain embodiments, the dosage of oral MSM ranges from about 1.0 to 2.5 g per day. In some embodiments, the dosage of oral MSM is 1.95 g per day. In other embodiments, MSM is administered (e.g., orally) in a dosage of up to about 6 g/day. These doses are well below the range of toxicity determined for MSM. At this dosage level, MSM reduces inflammation and radiological changes in the joint in several embodiments.

In certain embodiments, the synergistic effects between DMSO and MSM reduce the concentration of DMSO and/or MSM required to function as an effective anti-inflammatory or to generate analgesic effects. In certain embodiments, the synergy reduces the concentration of DMSO and/or MSM required to prevent structural changes to affected joints, the articular cartilage of joints and the juxtaposed subchondral bone. In several embodiments, DMSO functions to facilitate the activity of MSM (e.g., analgesia, anti-inflammatory effects, and the like). In some embodiments, DMSO provides further positive effects on the same aspects of a disease or condition that MSM positively impacts. Thus, in some embodiments, DMSO supplements and also facilitates the actions of MSM.

Further, the synergistic effects of certain embodiments reduce the amount of time from inception of treatment to amelioration of osteoarthritis symptoms. In some embodiments, this time period is reduced several fold, for example from the order of several months down to the order of several weeks. In certain embodiments, the synergistic effects result in symptomatic improvement within about 2 to 6 weeks.

In several embodiments, a formulation comprising DMSO and MSM lowers the amount of MSM required orally. In one embodiment, DMSO allows MSM to penetrate skin more effectively. According to some embodiments, the combination permits lower amounts of both DMSO and MSM to be used therapeutically, and optionally lowers odor, gastrointestinal symptoms, and/or the size of the capsule (or pill, tablet, or other dosage format). In one embodiment, MSM binds with DMSO metabolites for further odor reduction. In some embodiments (e.g., liquid forms for children), a flavor is added to DMSO and MSM to improve taste. Formulations comprising DMSO and/or MSM may also be added to therapeutic confectionaries, such as chews and gummies.

The synergism of DMSO and MSM according to several embodiments, allows reductions in the concentrations needed to effectively reduce osteoarthritis symptoms. In certain embodiments, the MSM functions as a skin protectant and unexpectedly protects the skin from the adverse effects of DMSO exposure. In some embodiments, topical MSM functions primarily as an inactive ingredient, e.g., it functions primarily to minimize dermal irritation that may otherwise be induced by topical DMSO administration. In some embodiments, MSM functions as a lubricant for the skin (e.g., to prevent excessive drying of the skin). In certain embodiments, the efficacious concentration of DMSO for lower limb joint treatment is reduced to 50% DMSO, or lower. In certain embodiments, the efficacious concentration of DMSO for upper limb joint treatment is reduced to 25-50% DMSO. In some embodiments, the duration that the skin is exposed to DMSO is reduced, because the DMSO/MSM formulation is more efficacious than DMSO alone. Thus, in certain embodiments, the DMSO/MSM topical formulation is left on the skin for 2-15 minutes and then removed (e.g., washed off). In other embodiments, DMSO/MSM topical formulation is left on the skin for about 5-10 minutes and then removed (e.g., washed off). In such embodiments, the possibility of side effects from DMSO exposure is reduced due to the reduction in exposure time and the protectant effects of MSM. However, in further embodiments, DMSO/MSM topical formulation is left on the skin and not removed. In some embodiments, DMSO and/or MSM act as antioxidants.

In several embodiments, the penetrant effect of DMSO allows MSM to achieve greater skin penetration and absorption, allowing enhanced anti-inflammatory effects. In some embodiments, the DMSO/MSM topical formulation unexpectedly provides analgesic effects. Further, the synergism exhibited by DMSO and MSM in the topical formulations can improve osteoarthritis symptoms in as little as about ½ a day to about 3 days, according to several embodiments. In some embodiments, DMSO and/or MSM are analgesic when provided in an oral dosage form.

In some embodiments, the synergism of DMSO and MSM, and the associated reduction in doses of both compounds, enables the simultaneous use of both oral and topical formulations. The reduced concentrations of DMSO and MSM (as compared to therapies of either DMSO or MSM alone), according to several embodiments described herein, reduce the overall occurrence of side effects and thereby enable simultaneous use of oral and topical formulations. Such embodiments therefore allow use of a topical formulation to ameliorate any acute joint pain, while the oral formulation serves to lower inflammation and pain on a chronic basis with minimal complications.

In some embodiments, the combination of DMSO and MSM and/or the use of solidified DMSO unexpectedly reduces the unpleasant odor normally experienced with DMSO use. For example, in certain embodiments, formulations comprising DMSO and MSM produce no perceptible odor after use. In some embodiments, a formulation comprising 10%-50% MSM reduces or eliminates the odor of DMSO provided at a concentration of 50%-90%. Previously, DMSO used at concentrations approaching 50% (or more) were associated with a strong unpleasant odor that could be detected through the skin or on the breath of a patient. Thus, several embodiments of the compositions described herein are unexpectedly advantageous because they reduce or eliminate the odor-related side effect.

According to any of the embodiments disclosed herein, a therapeutic system comprising MSM and DMSO, individually or combined, also includes one or more of the following compounds: ibuprofen, fenoprofen, indomethacin, naproxen, tolmetin, salicylic acid, and sulindac. In other embodiments, a therapeutic system comprising DMSO and/or MSM also includes one or more of the following compounds: antioxidants, glucosamine, chondroitin, niacinamide, S-adenosylmethionine, curcumin, quercetin, omega-3 fatty acids, papain, hyaluronic acid, and bromelain. In several embodiments, a formulation comprising DMSO and/or MSM and about 500-2500 mg glucosamine is provided. One or more of the following compounds may be used in addition to, or in place of, glucosamine: about 500-5000 mg fish oil, about 500-5000 IU Vitamin D, about 500-2500 mg chondroitin, 500-5000 mg or IU antioxidants (such as vitamin C, E or beta-carotene), about 500-2500 mg curcumin, and about 50-2500 mg hyaluronic acid. In some embodiments, formulations comprising DMSO and/or MSM inhibit the secretion of pro-inflammatory enzymes that are contribute to the breakdown of cartilage, including collagenase, hyaluronidase, and elastase. In some embodiments, formulations consisting or consisting essentially of DMSO and/or MSM inhibit the secretion of pro-inflammatory enzymes that are contribute to the breakdown of cartilage.

In several embodiments, a formulation comprising DMSO and/or MSM without a gastroprotectant is provided. Thus, several embodiments of the invention are particularly advantageous because it is estimated that many severe arthritic patients who are receiving NSAIDs are also co-prescribed a gastroprotectant.

In certain embodiments, the amount of DMSO in a topical formulation ranges from about 0.01% by weight to about 70% by weight. In other embodiments, the formulation comprises between about 0.01% and 10% DMSO by weight, and overlapping ranges thereof. Other embodiments comprise between about 10% and 20% DMSO, about 20-30% DMSO, about 30-40% DMSO, about 40-50% DMSO, about 50-60%, or about 60-70% DMSO, and overlapping ranges thereof. Still other embodiments comprise a formulation comprising between about 7% and 15% DMSO, about 15-25% DMSO, about 25-35% DMSO, about 35-45% DMSO, about 45-55% DMSO, about 55-60%, about 60-65%, or about 65-70%, and overlapping ranges thereof. In certain embodiments, DMSO is present in a range between about 45-55% by weight, including 45, 46, 47, 48, 49, 50, 51, 52, 53, 54, and 55%, and overlapping ranges thereof. In some embodiments, DMSO is provided in a range from about 70% to about 90%. Higher concentrations of DMSO may also be used in other embodiments.

In certain embodiments, the amount of MSM in a topical formulation ranges from about 0.01% by weight to about 70% by weight. In some embodiments, the formulation comprises between about 0.01% and 10% MSM by weight, and overlapping ranges thereof. Other embodiments comprise a formulation comprising between about 10% and 20% MSM, about 20-30% MSM, about 30-40% MSM, about 40-50% MSM, about 50-60%, or about 60-70% MSM, and overlapping ranges thereof. Still other embodiments comprise between about 7% and 15% MSM, about 15-25% MSM, about 25-35% MSM, about 35-45% MSM, or about 45-55% MSM, and overlapping ranges thereof. In certain other embodiments, MSM is present in a range between about 5-15% by weight, including 5, 6, 7, 8, 9, 10, 11, 12, 13, 14, and 15%, and overlapping ranges thereof. In some embodiments, MSM is provided in a range from about 70% to about 90%. Higher concentrations of MSM may also be used in other embodiments. In several embodiments, the percentages above are based on the volume of MSM used in an embodiment.

In several embodiments, a topical formulation MSM and DMSO, individually or combined, is provided in a concentration sufficient for application to the body in a thin layer. In one embodiment, the DMSO/MSM formulation is wiped across the surface of a joint in a thin layer and removed about five to ten minutes later with, for example, a wet wash cloth. In one embodiment, the target tissue (e.g., skin of the knee or other joint) is cleaned to deter the penetration of contaminants by DMSO. In some embodiments, volumes of the topical formulation applied range from about 0.5 mL to about 10 mL, depending on the tissue to which the formulation is applied. Thus, in some embodiments, the amount of the topical formulation applied in one use is between about 0.5 mL to about 1 mL, about 1 mL to about 3 mL, about 3 mL to about 5 mL, about 5 mL to about 7 mL, about 7 mL to about 10 mL, about 10 mL to about 20 mL, and overlapping ranges thereof. In some embodiments, a formulation comprising MSM, DMSO, or a combination of MSM and DMSO is provided in a topical formulation and a user is instructed to apply about 3 mL to about 15 mL per application per body part (e.g., knee).

In several embodiments, the topical formulation comprising MSM and DMSO, individually or combined, further comprises one or more inactive ingredients including, among others, de-ionized water and various polymers (for example, carbopol 974 NF). Active ingredients may also be provided. In some embodiments, a formulation consisting or consisting essentially of MSM and DMSO, individually or combined, is provided.

In some embodiments, formulations comprising DMSO and urea, and optionally MSM are provided to reduce odor. In some embodiments, formulations comprising DMSO and sulfur-binding compounds are used to reduce odor. In some embodiments, formulations comprising DMSO and at least one odor-reducing nutrient are used to reduce odor. In several embodiments in which odor is reduced, odors associated with the oxidation, metabolism, degradation or other conversion of DMSO are reduced. For example, in one embodiment, odors associated with methylthiomethane (DMS) are reduced. In some embodiments, MSM is used to reduce the odor of DMS that is produced by bacterial transformation of DMSO waste that is disposed (e.g., into sewage systems).

In several embodiments in which odor is reduced, odors associated with the oxidation, metabolism, degradation or other conversion of DMSO are reduced. In some embodiments, odors are reduced through the binding of odiferous compounds. In some embodiments, odors are reduced by reducing the production of odor-causing compounds. In some embodiments, odors are reduced by increasing the degradation of odor-causing compounds. According to one embodiment, compounds such as MSM are provided to reduce the odor associated with DMSO use by reducing the formation of DMSO metabolites or by binding to DMSO metabolites (e.g., DMS).

In several embodiments, a combined topical and oral DMSO/MSM formulation is used to treat osteoarthritis of the knee. In some embodiments, the formulation is used to treat a condition in which the patient has both knee pain and osteophytes (bone spurs) visualized on radiographs or when the patient is 40 years of age (or older), has morning knee stiffness lasting 30 minutes or less, and crepitus (grating, crackling or popping sounds) is detectable on motion of the knee.

In several embodiments, a combined topical and oral DMSO/MSM formulation is used to treat osteoarthritis of the hand. In some embodiments, the formulation is used to treat a condition in which a patient has hand pain, aching or stiffness, hard tissue enlargement of two or more of 10 selected joints, fewer than three swollen metacarpophalangeal joints, and hard tissue enlargement of two or more distal interphalangeal joints. In other embodiments, the formulation is used to treat a condition in which a patient has deformity of two or more of 10 selected joints (second and third distal interphalangeal joints, the second and third proximal interphalangeal joints and the first carpometacarpal joints (of both hands).

In several embodiments, a formulation comprising DMSO and MSM, alone or combined, is used to treat one or more joints of a patient, including but not limited to the knee, toe, thumb, finger, ankle, spine, hip, shoulder or other joint. In some embodiments, a formulation comprising DMSO and MSM, alone or combined, is used to treat lower back pain (e.g., pain in or associated with spinal column).

According to any of the embodiments disclosed herein, a combined topical and oral formulation comprising MSM and DMSO, individually or combined, is used to treat cartilage degeneration and/or degeneration of subchondral bone. In some embodiments, the formulation prevents, halts or treats bone spur formations, calcified areas and/or other undesired formations. A combined topical and oral DMSO/MSM formulation may also be used to treat joint pain, tenderness, stiffness, creaking, locking of joints, and/or local inflammation. In several embodiments, a combined topical and oral DMSO/MSM formulation is used to positively affect one or more of the following measures: (i) Radiological testing for both the knee and hand; (ii) Likert pain index on resting for both the knee and hand; (iii) Fuchs swelling index for both the knee and hand; (iv) Range of motion for both the knee and hand (or other joint); (v) Visual analog scale-pain intensity (VAS-PI) with loading for both the knee and hand and VAS Patient global assessment; (vi) The Lequesne index for the knee; (vii) WOMAC (Western Ontario and McMaster Osteoarthritis) physical stiffness and pain scale for the knee; (viii) Functional Index for Hand Osteoarthritis; (ix) Grip strength measurement; and (x) Rescue medication usage. Improvements of about 5%-100% in the identified measures are provided according to several embodiments (e.g., improvements of about 10-25%, 25-50%, 50-75%, 75-100%, and overlapping ranges thereof). Improvements in pain and inflammation may also be accompanied by increased range of motion, grip strength and general ability to perform daily activities according to several embodiments.

In several embodiments, a formulation comprising MSM and DMSO, individually or combined, is used to treat weakness, inflammation and/or pain in the hand, knee, or other joint. The formulation can be administered orally, topically, orally, or both orally and topically.

According to any of the embodiments disclosed herein, an oral formulation comprising MSM and DMSO, individually or combined, is used exclusively (without the topical treatment). According to any of the embodiments disclosed herein, a formulation comprising MSM and DMSO, individually or combined, is provided in a form suitable for administration intravenously, intra-articularly, and/or via inhalation in addition to or instead of oral administration. In some embodiments, the formulation is administration intravenously, intra-articularly, and/or via inhalation in addition to or instead of topical administration.

In several embodiments, subjects treated with a formulation comprising MSM and DMSO, individually or combined, include humans, non-human mammals, domesticated animals and livestock. In some embodiments, a formulation comprising MSM and DMSO, individually or combined, is used to not only treat undesired symptoms and illnesses, but can also act as a preventative. For example, an oral and/or topical formulation comprising MSM and DMSO, individually or combined, may be taken on a regular basis to prevent the onset of illness. Reversal of osteoarthritis is provided in several embodiments, while in other embodiments, formulations comprising MSM and DMSO, individually or combined, prevent the onset or progression of the disease.

Formulations Comprising Solid DMSO

In several embodiments, a formulation comprising solid DMSO, alone or in combination with MSM, is provided. Pure DMSO is typically a clear and colorless dipolar liquid at room temperature with a melting point of 18.4° C. (or 65° F.), a flash point of 95° C., and a boiling point of 189° C. at sea level. It is an aprotic and very hygroscopic chemical with a molecular weight of 78.13. However, application or ingestion of DMSO often yields an unpleasant odor, which "tastes" like garlic shortly after it contacts the skin. In addition, irritation, dryness, redness and/or itching of the skin can develop where DMSO is applied topically in repeated doses or in high concentrations. Other side effects of DMSO can include sensitivity to light, visual disturbances, headache, nausea, upset stomach, and diarrhea. Side effects, such as allergic reactions to DMSO, can occur in certain cases, e.g., palpitations, arrhythmias, and/or respiratory issues. Undesired effects of DMSO may be caused by DMSO, its metabolism, catalysis, oxidation, degradation, and/or other conversion. Due to its physical properties, DMSO is typically utilized in its liquid form.

MSM is an organosulfur compound that is a metabolite of DMSO and certain sulfur-containing amino acids. It is a white, water-soluble powder with a melting point of 109° C., a flash point of 143° C., and a boiling point of 248° C. It has a molecular weight of 94.13.

Due to its physical properties, DMSO exists as a liquid at room temperature, and is therefore typically utilized as a liquid. However, there is a long felt and as yet unmet need for a solid form of DMSO at room temperature. For example, solid forms of DMSO are particularly advantageous because they (i) are able to be manufactured or packaged into pill, tablet or capsule form; (ii) are able to achieve concentrated forms (about 2-50 fold more concentrated than liquid forms per dose size); (iii) exhibit reduced side effects as compared to the liquid form (e.g., less irritation, sensitivities, gastrointestinal effects, etc.); and (iv) exhibit reduced or no odor as compared to the liquid form. In some embodiments, the use of DMSO that stays solid at room temperature is particularly advantageous because it permits the inclusion of DMSO into capsules (or other packaging) that would normally be degraded by liquid DMSO.

In some embodiments, DMSO that is solid at room temperature is provided. In some embodiments, DMSO that is solid at temperatures between 70-80° F., 80-90° F., 90-100° F., 100-125° F., and higher than 125° F. is provided. In other embodiments, DMSO that is solid at room temperature is provided, wherein said DMSO liquefies at about 65° F.

In accordance with certain embodiments, surprisingly, the combination of DMSO and MSM yields a solid form of DMSO at room temperature. In some embodiments, DMSO and MSM are combined by mixing hydrogen peroxide with a liquid form of DMSO. In these embodiments, the hydrogen peroxide and DMSO are heated. In some embodiments, MSM is formed, but not all of the DMSO is removed. In certain other embodiments, DMSO and MSM are combined by mixing a liquid form of DMSO in a MSM solution. In these embodiments, the solution can be heated and agitated. In some embodiments, DMSO and MSM are combined by mixing a solid form of MSM in a liquid form of DMSO. In other embodiments, DMSO and MSM are combined by mixing a liquid form of DMSO with a molten form of MSM.

In one embodiment, liquid DMSO is used as a starting material. The liquid form of DMSO is mixed with hydrogen peroxide ($H_2O_2$) at a temperature and time sufficient for substantially all of the hydrogen peroxide to be consumed and for MSM and water by-product to form. In certain embodiments, not all of the DMSO is removed, thereby yielding a molten DMSO/MSM combination that may subsequently be cooled. For example, in one embodiment, liquid DMSO at a concentration of about 90-100% is combined with 30% to 51% $H_2O_2$ at stoichiometric ratio and a temperature of about 230-250° F. until at least 90% of the $H_2O_2$ is consumed, and a product containing about 0.1%-15% DMSO and 85%-99.9% MSM is produced. Extreme caution must be maintained as this is an extremely exothermic reaction.

In several embodiments, the preparation of MSM involves a high temperature distillation step which results in molten MSM. In such embodiments, DMSO may be added back into the molten MSM in known quantities under agitation. In some embodiments, the DMSO added back is in liquid form, while in other embodiments, the DMSO is in solid form. The resultant DMSO/MSM combination is further agitated and then rapidly cooled in one embodiment.

In one embodiment, the molten DMSO/MSM combination is sent to a spray cooler/prilling chamber to form solid prills or microprills (microspherical pellets). In certain embodiments, the molten DMSO/MSM combination is fed into the prilling chamber where the molten DMSO/MSM combination enters a droplet generator to discharge the material in the form of droplets. As the droplets fall freely, they are cooled and solidify into spheres or prills. The spheres or prills have a diameter in the range of about 75 microns to 840 microns (e.g., about 75-150 microns, about 150-300 microns, about 300-450 microns, about 450-600 microns, about 600-840 microns, and overlapping ranges therein).

In certain embodiments, the droplets are cooled with a flow of cold gas, such as but not limited to air, nitrogen gas, or carbon dioxide. In certain other embodiments, the droplets are cooled with a spray of cold water or cold liquid nitrogen. In other embodiments, the droplets are cooled by dry ice. In accordance with certain embodiments described herein, after the droplets are cooled, since the exteriors of the droplets cool first, the prills can remain in the cool temperature to solidify the interiors of the prills.

In certain other embodiments, the molten DMSO/MSM combination (e.g., mixture) is sent to a flaking system to form solid flakes. For example, in one embodiment, the molten DMSO/MSM combination is sent to a drum flaker, where a thin warm layer of the molten DMSO/MSM combination is applied to the outside of a rotating drum. As the drum rotates, a cooling agent housed within the rotating drum cools and solidifies the layer of material on the exterior of the drum, and a knife scraper removes the material in the shape of flakes. Various cooling agents can be used, for example, liquid nitrogen, liquid oxygen, cooled water, or cooled water containing polypropylene glycol.

In accordance with several embodiments described herein, MSM can be purified prior to combining it with DMSO. In some embodiments, purification is accomplished by distillation, among other methods. In certain embodiments, DMSO powders or flakes are combined with MSM prill. In other embodiments, DMSO powders or flakes are combined with MSM flakes. In other embodiments, DMSO powders or flakes are combined with MSM powder. In certain embodiments, a homogenous mixture of DMSO/MSM is produced, while in other embodiments, a non-homogenous mixture results.

In accordance with several embodiments described herein, MSM may be combined with DMSO to form a DMSO/MSM solution, and the resultant mixed solution is subsequently frozen and ground into powder. In some embodiments, the liquid phase of the DMSO/MSM solution is water. In some embodiments, distilled, deionized, or distilled-deionized water is used. In other embodiments, other liquids may used. For example, the DMSO/MSM solution may contain normal saline, or another acceptable solvent. In certain embodiments, the ionic characteristics of the liquid may be adjusted to affect the resultant DMSO/MSM product. In some embodiments, other ingredients are added into the solution, with the solution heated and agitated to facilitate mixing. The DMSO/MSM solution can be cooled and frozen. For example, the liquid DMSO can be cooled in a cooling chamber containing cold gas, such as but not limited to air, nitrogen gas, or carbon dioxide. The DMSO/MSM combination is then ground by any grinding or milling technique well known in the art or yet to be devised.

In other embodiments, DMSO is added to molten MSM. In certain embodiments, the DMSO/MSM combination is formed into a solid by a spray cooler/prilling chamber as described above. In other embodiments, the DMSO/MSM combination is formed into a solid by a flaking system as described herein.

In some embodiments, the purity of the starting raw materials can be altered to adjust the purity of the end product. Depending on the level of purity required, one or more purification processes may be employed. For example, in some embodiments where DMSO is the starting material, impurities can exist because DMSO is a strong solvent. Thus, the starting MSM and/or DMSO may be purified prior to the manufacture of the DMSO/MSM combination. In some embodiments, the synthesis of MSM from DMSO yields side reactions and compounds. In some embodiments, additional purification can be performed after the DMSO/MSM product is formed.

In one embodiment, distillation is employed as the purification process. Other contaminant/by-product removing procedures may be used instead of, or in addition to, distillation. Distillation removes the water and contaminates from the raw materials and from side reactions. In accordance with some embodiments described herein, distillation can form a molten MSM into which DMSO may be added. In some embodiments, the DMSO/MSM combination is tested after production to reduce potential hazardous heavy metals, such as lead, mercury, cadmium, and arsenic, to levels below specified standards.

In some embodiments, gelatin and/or hydroxypropyl methylcellulose (HPMC) is used with the organic based solvent system to form a gel-cap. In other embodiments, the organic based solvent system is used to form a tablet. In some embodiments, the tablet is uncoated. In some embodiments, the tablet is coated. In certain embodiments, the coating is pH stable and provides a time-release effect, such that the tablet is positioned in a portion of the gastrointestinal tract that is highly absorptive, such as the ileum.

In several embodiments, the organic based solvent system is used to formulate an orally consumable effervescent DMSO/MSM formulation, allowing for enhanced absorption of DMSO and MSM. For example, in certain embodiments, a DMSO/MSM powder is produced that when added to a consumable liquid, dissolves and yields and effervescent beverage for consumption. In certain embodiments, the DMSO/MSM powder is pre-packaged into single-dose serving sizes. In other embodiments, formulations comprising DMSO and MSM, alone or combined, are formulated into a tablet that can similarly be dissolved to produce an effervescent beverage. Any consumable liquid may be used to dissolve, the powder or tablet, with the taste of the liquid being driven by the choice of the consumer. In other embodiments, flavors may be added to the DMSO and/or MSM powder or tablet, such that, when combined with water, a flavored effervescent beverage results.

In accordance with some embodiments described herein, a DMSO/MSM active capsule is produced. In one non-limiting example, prior to or during the process to form the DMSO/MSM combination into a solid, vegetable coating, amorphous silicon dioxide, and magnesium stearate are blended and added into the DMSO/MSM combination to produce a formulation comprising 650 mg of MSM, 15 mg of DMSO, 285 mg of Dritex-S Flake coating, 4.75 mg of silicon dioxide, and 4.75 mg of magnesium stearate. The vegetable coating may be fully hydrogenated soybean oil that has been further processed into flake form such as Dritex-S flakes and used as an encapsulating agent. A placebo capsule can also be produced with a formulation consisting of 1 mg of DMSO, 950 mg of Pac-Gel 70, 4.75 mg of silicon dioxide, and 4.75 mg of magnesium stearate. In several embodiments, as discussed herein, greater or lesser percentages of MSM and/or DMSO are used for active oral formulations. Placebos are also adjusted accordingly. In some embodiments, multilayer emulsions are provided as coating materials. In one embodiment, nano-laminated lipids are used as coating materials. Polymers are used in some embodiments. In some embodiments, coatings comprise hydrogels, gelatins, soybean oil, malitol, or combination thereof.

In accordance with certain embodiments described herein, topical formulations, e.g., gels, lotions, and creams, can be produced by mixing DMSO into a MSM solution. In some embodiments, distilled, deionized, or distilled-deionized water is used. In other embodiments, other liquids may used. For example, the MSM solution may contain normal saline, or another acceptable solvent. In certain embodiments, other ingredients such as thickening agents, emulsifiers, and fragrances, used in topical formulations which are well known in the art or yet to be devised can be mixed into the solution. In certain embodiments, the solution is heated and agitated to facilitate dissolution. Once mixed, the solution is allowed to cool to form a gel, lotion or cream in some embodiments.

In one embodiment, an active topical gel is produced. In one non-limiting example, 50 ml of de-ionized water is warmed on a hot plate. MSM (12 g) is added to the warm water and dissolved. After complete dissolution of the MSM, DMSO (60 g) is added to the MSM solution. Cross-linked acrylic acid polymer (Carbopol 974 NF) is added to the solution with constant agitation, which serves to wet the polymer as it is being added. The temperature of the solution is brought to between about 50-60° C. and agitation is continued until the polymer is completely dissolved. Sodium carbonate ($Na_2CO_3$, 0.02 g) is dissolved in an additional 10 mL of deionized water. Once the $Na_2CO_3$ is completely dissolved, it is added to the DMSO/MSM/polymer solution with simultaneous stirring by hand. Once thoroughly mixed, the solution is allowed to cool, resulting in a viscous gel of containing 50% DMSO/10% MSM with 1% Carbopol 974 NF and 39% de-ionized water. Viscosity is measured at approximately 300,000 cPs at 23° C. (73° F.). In several embodiments, as discussed herein, greater or lesser percentages of MSM and/or DMSO are used for topical formulations. In several embodiments, percentages of DMSO and/or MSM are by volume, as stated, rather than by weight.

In certain embodiments described herein, formulations comprising DMSO and MSM, alone or in combination, are provided the form of a capsule, a gel-cap, a tablet, oral suspension, a powder, or an effervescent. Gels, slurries, particles, powders and other dehydrated forms are also provided in some embodiments. In certain embodiments, a formulation comprising DMSO and MSM that is not liquid (e.g., a solid) at room temperature is provided. In some embodiments, solid formulations are advantageous in that they maintain their consistency, e.g., maintain one or more of a hardness, firmness, density, texture, and/or viscosity that is at least 75%, 85%, 95% or 100% the same, over a wide range of temperatures (e.g., from about 0° C. to about 100° C., about 5° C. to about 50° C., about 10° C. to about 40° C., about 20° C. and about 30° C., and overlapping ranges thereof). Certain embodiments are covered with a coating while other embodiments are not coated. Where a coating is provided, the coating may render a time-release effect. In certain embodiments, DMSO is between about 0.01% to about 10% by weight of the formulation. In several embodiments, the percentages above are based on the volume of DMSO used in an embodiment.

In several embodiments, a solid formulation comprising DMSO is used in several industrial and medical applications. In some embodiments, solid DMSO is used for storing and transporting DMSO.

In several embodiments, the amount of DMSO in a solid formulation comprising DMSO and MSM (and optionally other ingredients) ranges from about 0.01% by weight to about 90% by weight. In other embodiments, the formulation comprises between about 0.01% and 10% DMSO by weight. In certain embodiments DMSO is present in about 0.01% to about 5%, about 0.01% to about 2.5%, or 0.01% to about 2.0%. In some embodiments, DMSO is present in about 0.5% to about 1.75%, including 0.6, 0.7, 0.8, 0.9, 1.0, 1.1, 1.2, 1.3, 1.4, 1.5, 1.55, 1.6, 1.65, 1.7, and 1.75%, and overlapping ranges thereof. Other embodiments comprise a formulation comprising between about 10 and 20% DMSO, about 20-30% DMSO, about 30-40% DMSO, about 40-50% DMSO, about 50-60% DMSO, about 60-70% DMSO, about 70-80% DMSO, about 80-90% DMSO. Still other embodiments comprise from about 7 to about 15% DMSO, about 15-25% DMSO, about 25-35% DMSO, about 35-45% DMSO, about 45-55% DMSO, about 55-65% DMSO, about 65-75% DMSO, or about 75-85% DMSO, and overlapping ranges thereof. Several embodiments for capsules, gel-caps, powders, and effervescents comprise between about 0.01-10% DMSO, including 0.5, 1, 2, 3, 4, 5, 6, 7, 8, and 9% DMSO. Several embodiments for gels, lotions, and creams comprise DMSO at a concentration of between 30% and 90%, for example, about 45-55%.

In several embodiments, the amount of MSM in a solid formulation comprising DMSO and MSM (and optionally other ingredients) ranges from about 0.01% by weight to about 70% by weight. In other embodiments, the formulation comprises between about 0.01% and 10% MSM by weight. Other embodiments comprise between about 10 and 20% MSM, about 20-30% MSM, about 30-40% MSM, about 40-50% MSM, about 50-60% MSM, or about 60-70% MSM including 60, 61, 62, 63, 64, 65, 66, 67, 68, 69, and 70% MSM, and overlapping ranges thereof. Still other embodiments comprise a formulation comprising about 7 and 15% MSM, about 15-25% MSM, about 25-35% MSM, about 35-45% MSM, about 55-60% MSM, about 60-65% MSM, or about 65-70% MSM, and overlapping ranges thereof. Some embodiments for capsules, gel-caps, powders, and effervescents comprise between about 90-99% MSM, including 91, 92, 93, 94, 95, 96, 97, and 98% MSM. Several embodiments for gels, lotions, and creams comprise between about 5 to 15% MSM.

In some embodiments, the solid formulation is uncoated. In other embodiments, the solid formulation is covered with a coating. In some embodiments, the coating provides a time-release effect (e.g., sustained-release, sustained-action, extended-release, controlled-release, or continuous-release).

Coatings, in some embodiments, incorporate a flavor additive, such that there is no chalky or medicinal-tasting residue remaining after consuming the solid formulation. As used herein, "solid" shall be given its ordinary meaning and shall additionally refer to semi-solids, gels, viscous solutions, and other compounds that are not in liquid or gaseous phases. Solidified DMSO, alone or in combination with MSM, may be provided in the form of oral capsules, gel-caps, tablets, powders, and effervescents, or topical gels, lotions, and creams. Other forms may also be manufactured. As used herein, "compound" shall be given its ordinary meaning and shall include, but not be limited to, molecules, ingredients, atoms, substances and elements.

In some embodiments, one or more additional agents are added into the DMSO/MSM combination. In certain embodiments, pharmaceuticals, including but not limited to analgesics and anti-inflammatory agents, are employed with the DMSO/MSM combination. In certain embodiments, antimicrobials, such as penicillin and antibiotics, can be employed with the DMSO/MSM combination. In certain embodiments, vitamins and supplements are added.

In several embodiments, a solid formulation comprising MSM and DMSO, individually or combined, is provided that optionally comprises one or more inactive ingredients including, among others, microencapsulating agents (for example Dritex-S Flake coating), silicon dioxide, and magnesium stearate. In several embodiments, a solid formulation comprising MSM and DMSO, alone or in combination, is encapsulated to, for example, facilitate delivery, bioactivity, absorption, time-release, and/or palatability. In several embodiments, non-encapsulated powders facilitate delivery, bioactivity, absorption, time-release, and/or palatability.

EXAMPLE

The following example is provided to further illustrate certain embodiments within the scope of the invention. The example is not to be construed as a limitation of any embodiments, since numerous modifications and variations are possible without departing from the spirit and scope of the invention.

Example 1

Absorption of MSM in Topical Formulation is within Recognized Safe Levels

Approximately 17% of DMSO is metabolized into MSM in the body. DMSO has been established to function as a penetration enhancer (among other functions). This study investigated the circulating concentrations of MSM when MSM is topically applied in combination with one of two concentrations of DMSO. According to the study, in some embodiments, MSM is not a pharmacologically active ingredient when applied topically. Rather, in some embodiments, topical MSM works synergistically with DMSO to reduce one or more side effects of DMSO. Thus, higher concentrations of DMSO (which would otherwise be prohibitive because of the undesired side effects) are able to be used to treat subjects.

New Zealand White rabbits, which are an accepted animal model for dermal absorption studies, were used to assess the absorption and resultant blood levels of MSM. Rabbits were obtained from Charles River Canada (Saint-Constant, Quebec). Five male rabbits, ages 12-13 weeks (and ranging in weight from 2.6 kg to 2.7 kg) were used for the dermal absorption studies. Rabbits were used because of their greater skin permeability as compared to rats, pigs or humans. Thus, testing on rabbits is a more conservative approach for the safety of topical products for human use. The size of rabbit was based on the ethical restriction of collecting greater than 6 mL/kg body weight of blood within a two week period. The total volume of blood to be removed during this study was 10 mL on a single day. One animal per group was used to minimize the number of animals required. Animals were housed individually in stainless steel cages with 12 hours light/dark cycles. The animal room environment was monitored daily (targeted ranges: 18-26° C. and relative humidity 25-50%). Fresh air was supplied to the room at a sufficient rate to provide approximately 15 to 17 changes of room air per hour. Clinical observations were conducted for all animals to ensure animals were in good health prior to dosing. Morbidity and mortality observations were also conducted during the study period.

Treatment groups were as shown in Table 1:

TABLE 1

Study 1 Design

| Group | Test Article | Surface Area Exposed | Volume Applied | Number of Animals | Blood Collection Times (min) |
|---|---|---|---|---|---|
| A | 10% MSM + 90% Water | 6 cm² | 0.5 mL | 1 | 0 (pre-dose), 10, 30, 120, 480 minutes |
| B | 50% DMSO + 50% Water | 6 cm² | 0.5 mL | 1 | 0 (pre-dose), 10, 30, 120, 480 minutes |
| C | 70% DMSO + 30% Water | 6 cm² | 0.5 mL | 1 | 0 (pre-dose), 10, 30, 120, 480 minute |
| D | 10% MSM + 50% DMSO + 40% Water | 6 cm² | 0.5 mL | 1 | 0 (pre-dose), 10, 30, 120, 480 minutes |
| E | 10% MSM + 70% DMSO + 20% Water | 6 cm² | 0.5 mL | 1 | 0 (pre-dose), 10, 30, 120, 480 minutes |

One day prior to the experiment, the rump of each rabbit was closely clipped using hair clippers. An area of 6 cm² was measured and marked to ensure equivalence in the application of the various compositions. Each product was applied by pipetting 0.5 mL of each composition into the center of the test area and spread to cover the entire test area. After the 5 minute exposure period, the compositions were removed by wiping, rinsing and drying the test area.

Prior to blood collection, animals were tranquilized with Acepromazine (1 mg/kg) by intramuscular injection in the right hind leg muscle, after which EMLA cream (lidocaine/prilocaine) was applied to both ears along the ear artery. Blood was collected by insertion of a 21 G needle (hub removed) into the ear artery. Approximately 2 mL of whole blood was collected into 4 mL Vacutainer™ tubes (Becton Dickinson, Mississauga, ON) containing $K_2EDTA$. Tubes were inverted to mix with the anticoagulant and stored refrigerated until plasma was separated by centrifugation. Plasma was separated from whole blood by centrifugation at 3000×g for 10 minutes. Plasma was collected, transferred and stored in a cryovial at −70° C. until further processing for MSM analysis.

Following the 5 minute exposure period to the various test products (see Table 1), blood was collected after 10 minutes, 30 minutes, 2 hours and 8 hours. Prior to the 2 and 8 hour blood collections, EMLA cream was applied to the ears (approximately 30 minutes prior to each of these blood draws) as the anesthetic effects of the EMLA cream lasts approximately 1-2 hours. Both EMLA cream and Acepromazine were used due to ethical considerations and to provide for the well being of the animals used in this project.

The concentrations of MSM in plasma were quantified by Gas Chromatography-Mass Spectrometry (GC/MS) based on established methods. Briefly, 4504 of plasma sample was mixed with 50 μL of physiological saline and vortexed for 30 seconds. Following this 1 mL of Acetonitrile (Fisher, HPLC grade) was added to the mixture. The solution was vortexed vigorously for 60 seconds and centrifuged at 2000 rpm for 5 minutes. 1 μl, of the clear supernatant was introduced to the GC/MS system (GC/MS QP20108 EI, Shimadzu, Kyoto, Japan). The analysis was performed on a 8himadzu SHR5XLB column (0.25 mm ID×length 30 m, film 0.25 um, Kyoto, Japan). The retention time of MSM was 6.1-6.3 minutes. MSM was detected with MS and m/z 79 (M+−15) was used for monitoring MSM ion SIM profiles. Helium gas was used as the carrier gas, head pressure was 0.25 kg/cm2, make-up gas was 30 ml/min, column temperature was 80° C., injector temperature 120° C., separator temperature 200° C. and ion source temperature 250° C. The ionization energy was 70 eV. An external standard graph was prepared with MSM dissolved in acetonitrile at the following concentrations: 62.5 μg/ml, 31.3 μg/ml, 15.6 μg/ml, 7.8 μg/ml, 3.9 μg/ml, 1.9 μg/ml, 0.98 μg/ml and 0.49 μg/ml. The MSM concentration in plasma samples was calculated from the slope of the standard curve. The best fitted graph was linear with a R2 value of 0.998.

All animals were observed prior to the start of the experiment and all demonstrated good health. During the course of the experiment and subsequent to the experiment, all animals demonstrated good health. Morbidity, mortality and injury were assessed twice daily. No animals demonstrated any morbidity, mortality or injury.

Figure 2:
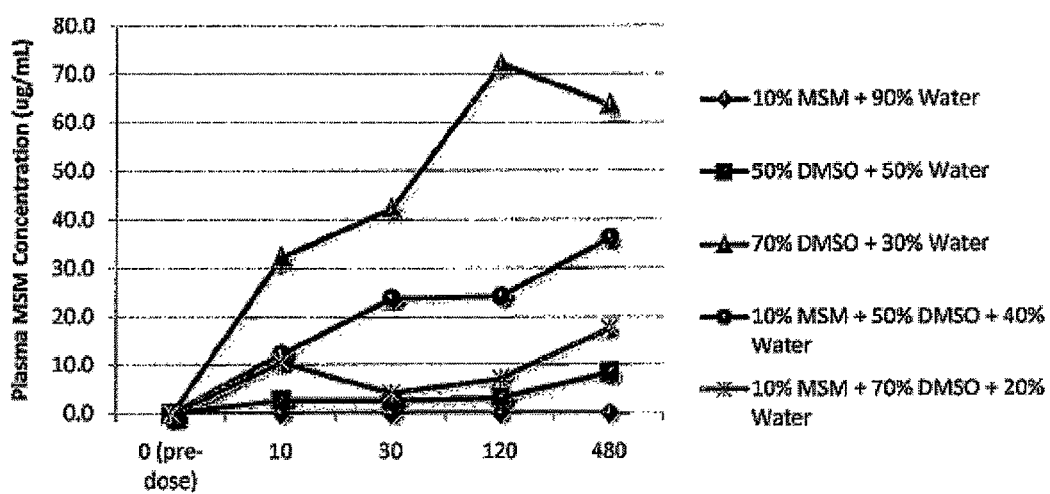
FIG. 2 depicts the change from baseline of the MSM plasma concentrations.

The results of the absorption study are summarized in Table 2 and graphically depicted in FIGS. 1 and 2. Baseline plasma concentrations of MSM (prior to exposure to test articles) ranged between 4.2 μg/mL and 104.2 μg/mL (see FIG. 1). The variation in, baseline is within the normal range of variation of natural MSM concentrations that have been established in prior studies. Following exposure to the various test articles, the highest plasma concentrations of MSM measured were less than or equal to approximately 140 μg/mL (see FIG. 1). This peak concentration results from exposure to 10% MSM+70% DMSO+20% water. When corrected for natural variation in baseline MSM concentrations, the largest change in plasma MSM was detected in the 70% DMSO+30% water group. These data suggest that variations in MSM, either due to absorption or due to metabolism of DMSO, are within the natural range of MSM concentrations.

As such, in several embodiments, MSM is an inert ingredient in topical applications, with respect to analgesic function. However, as discussed herein, MSM does provide several beneficial effects. In several embodiments, MSM functions to reduce the side effects normally associated with DMSO (skin effects, odor, etc.). In several embodiments, MSM functions as an emollient, which also may aid in reducing irritation of the skin by DMSO. As such, the combination of MSM with DMSO in the topical formulation embodiments described herein allow for the use of concentrations of DMSO that function to reduce one or more symptoms of osteoarthritis without the normal array of DMSO-associated side effects. Thus, in certain embodiments, the presence of MSM advantageously allows for the unexpected use of higher (and more efficacious) concentrations of DMSO without the side effects.

TABLE 2

Concentration of MSM in Plasma
After Exposure to MSM and DMSO

| Treatment | Time point (minute) | MSM Concentration (μg/mL) |
|---|---|---|
| 10% MSM + 90% water | 0 | 25.6 |
|  | 10 | 17.6 |
|  | 30 | 16.3 |
|  | 120 | 14.0 |
|  | 480 | 15.4 |
| 50% DMSO + 50% water | 0 | 4.2 |
|  | 10 | 6.9 |
|  | 30 | 6.9 |
|  | 120 | 7.4 |
|  | 480 | 12.6 |
| 70% DMSO + 30% water | 0 | 56.7 |
|  | 10 | 89.0 |
|  | 30 | 98.9 |
|  | 120 | 128.7 |
|  | 480 | 120.2 |
| 10% MS M + 50% DMSO + 40% water | 0 | 104.2 |
|  | 10 | 116.5 |
|  | 30 | 127.9 |
|  | 120 | 128.4 |
|  | 480 | 140.4 |
| 10% MSM + 70% DMSO + 20% water | 0 | 26.8 |
|  | 10 | 37.3 |
|  | 30 | 30.9 |
|  | 120 | 33.9 |
|  | 480 | 44.4 |

It will be understood by those of skill in the art that numerous and various modifications can be made without departing from the spirit of the embodiments of the present invention. Method steps described herein need not be performed in the order set forth. It should be clearly understood that embodiments disclosed herein are illustrative only and are not intended to limit the scope of the present invention.

What is claimed is:

1. A kit comprising: a solid oral formulation comprising about 5 mg to about 50 mg dimethylsulfoxide (DMSO) and about 300 mg to about 800 mg methylsulfonylmethane (MSM) as prills, microprills, or flakes prepared by flacking, prilling and/or freezing a liquid combination of DMSO and MSM, wherein the prills, microprills, or flakes have a diameter of about 75 microns to about 840 microns and stay solid at room temperature; and a topical formulation comprising about 40% to about 90% dimethylsulfoxide (DMSO) and about 1% to about 50% methylsulfonylmethane (MSM), wherein the topical formulation is provided in a gel, cream, serum, liquid, spray, ointment, and/or patch form.

2. The kit of claim 1, wherein the liquid combination is prepared by heating a combination of liquid DMSO and solid MSM.

3. The kit of claim 1, wherein the solid oral formulation comprises about 30 mg to about 50 mg DMSO and about 500 mg to about 800 mg MSM.

4. The kit of claim 1, wherein the topical formulation has a weight ratio of MSM to DMSO of about 1:2-10.

* * * * *